(12) United States Patent
Lustbader

(10) Patent No.: US 7,081,446 B2
(45) Date of Patent: Jul. 25, 2006

(54) LONG-ACTING FOLLICLE STIMULATING HORMONE ANALOGUES AND USES THEREOF

(75) Inventor: Joyce Lustbader, Tenafly, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 323 days.

(21) Appl. No.: 10/112,321

(22) Filed: Mar. 27, 2002

(65) Prior Publication Data
US 2003/0143694 A1 Jul. 31, 2003

Related U.S. Application Data

(63) Continuation-in-part of application No. 10/062,910, filed on Jan. 31, 2002, now abandoned.

(51) Int. Cl.
| | |
|---|---|
| A61K 38/16 | (2006.01) |
| A61K 38/00 | (2006.01) |
| A61K 38/02 | (2006.01) |
| C07K 2/00 | (2006.01) |
| C07K 7/08 | (2006.01) |

(52) U.S. Cl. .................. 514/13; 530/300; 530/326; 514/2

(58) Field of Classification Search .................. 514/2; 530/300, 326
See application file for complete search history.

(56) References Cited

U.S. PATENT DOCUMENTS

| | | | |
|---|---|---|---|
| 5,585,345 A | 12/1996 | Boime | |
| 5,712,122 A * | 1/1998 | Boime et al. | ............... 435/69.7 |
| 5,759,818 A | 6/1998 | Boime | |
| 5,958,737 A | 9/1999 | Boime et al. | |
| 5,985,611 A | 11/1999 | Boime | |
| 6,225,449 B1 | 5/2001 | Boime | |
| 6,242,580 B1 * | 6/2001 | Boime et al. | ............... 530/398 |
| 6,306,654 B1 | 10/2001 | Boime et al. | |

OTHER PUBLICATIONS

Bishop, et al. Endocrinology. (1995), 136(6), pp. 2635-2640.*
G.D. Duffaud, et al. Methods in Enzymology. (1987) 153, pp. 492-507.*
Bouloux, P. M., D. J. Handelsman, F. Jockenhovel, E. Nieschlag, J. Rabinovici, W. L. Frasa, J. J. de Bie, G. Voortman, and J. Itskovitz-Eldor (2001) First human exposure to FSH-CTP in hypogonadotrophic hypogonadal males. *Hum. Reprod.* 16, 1592-1597 (Exhibit 7).
Calvo, F. O., H. T. Keutmann, E. R. Bergert, and R. J. Ryan (1986) Deglycosylated human follitropin: characterization and effects on adenosine cyclic 3',5'-phosphate production in porcine granulosa cells. *Biochemistry* 25, 3938-3943 (Exhibit 8).
Chui, D. K., N. D. Pugh, S. M. Walker, L. Gregory, and R. W. Shaw (1997) Follicular vascularity—the predictive value of transvaginal power Doppler ultrasonography in an in vitro fertilization programme: a preliminary study. *Hum. Reprod.* 12, 191-196 (Exhibit 9).
Dissen, G. A., H. E. Lara, W. H. Fahrenbach, M. E. Costa, and S. R. Ojeda (1994) Immature rat ovaries become revascularized rapidly after autotransplantation and show a gonadotropin-dependent increase in angiogenic factor gene expression. *Endocrinology* 134, 1146-1154 (Exhibit 10).
Fares, F. A., N. Suganuma, K. Nishimori, P. S. Lapolt, A. J. Hsueh, and I. Boime (1992) Design of a long-acting follitropin agonist by fusing the C-terminal sequence of the chorionic gonadotropin beta subunit to the follitropin beta subunit. *Proc. Natl. Acad. Sci. U.S.A.* 89, 4304-4308 (Exhibit 11).
Feng, W., M. M. Matzuk, K. Mountjoy, E. Bedows, R. W. Ruddon, and I. Boime (1995) The asparagine-linked oligosaccharides of the human chorionic gonadotropin beta subunit facilitate correct disulfide bond pairing. *J. Biol. Chem.* 270, 11851-11859 (Exhibit 12).
Ferrara, N., H. Chen, T. Davis-Smyth, H. P. Gerber, T. N. Nguyen, D. Peers, V. Chisholm, K. J. Hillan, and R. H. Schwall (1998) Vascular endothelial growth factor is essential for corpus luteum angiogenesis. *Nat. Med.* 4, 336-340, (Exhibit 13).
Ferrara, N., K. Houck, L. Jakeman, and D. W. Leung (1992) Molecular and biological properties of the vascular endothelial growth factor family of proteins. *Endocr. Rev.* 13, 18-32 (Exhibit 14).
Krichevsky, A., S. Birken, J. F. O'Connor, K. Bikel, J. Schlatterer, and R. E. Canfield (1994) The development of a panel of monoclonal antibodies to human luteinizing hormone and its application to immunological mapping and two-site assays. *Endocrine 2.* 511-520 (Exhibit 15).
LeContonnec, J.Y., H.C. Porchet, V. Beltrami, A. Khan, S. Toon, and M. Rowland (1994) Clinical pharmacology of recombinant human follicle-stimulating hormone. II. Single doses and steady-state pharmacokinetics. *Fertil. Steril.* 61, 679-86 (Exhibit 16).
Lindau-Shapard, B.A., H.A. Brumberg, A.J. Peterson, and J.A. Dias (2001) Reversible immunoneutralization of human follitropin receptor. *J. Reprod. Immun.* 49, 1-19 (Exhibit 17).
Matzuk, M. M., A. J. Hsueh, P. Lapolt, A. Tsafriri, J. L. Keene, and I. Boime (1990) The biological role of the carboxyl-terminal extension of human chorionic gonadotropin beta-subunit. *Endocrinology* 126, 376-383 (Exhibit 18).

(Continued)

*Primary Examiner*—Bruce R. Campell
*Assistant Examiner*—Andrew D. Kosar
(74) *Attorney, Agent, or Firm*—John P. White, Esq.; Cooper & Dunham LLP

(57) ABSTRACT

This invention provides FSH analogues having increased serum half-life relative to FSH. This invention also provides related compositions and methods for increasing fertility, egg production and spermatogenesis in a subject.

29 Claims, 21 Drawing Sheets

OTHER PUBLICATIONS

Nargund, G., T. Bourne, P. Doyle, J. Parsons, W. Cheng, S. Campbell, and W. Collins (1996) Associations between ultrasound indices of follicular blood flow, oocyte recovery and preimplantation embryo quality. *Hum. Reprod.* 11, 109-113 (Exhibit 19).

Pedersen, T. and H. Peters (1968) Proposal for a classification of oocytes and follicles in the mouse ovary. *J. Reprod. Fertil.* 17, 555-557 (Exhibit 20).

Pierce, J. G. and T. F. Parsons (1981) Glycoprotein hormones: structure and function. *Annu. Rev. Biochem.* 50 465-495 (Exhibit 21).

Porchet, H.S., J.Y. LeContonnec, B. Neuteboom, S. Canali, and G. Zanolo (1995) Pharmacokinetics of recombinant human luteinizing hormone. *J. Clin. Endocrinol. Metab.* 80, 667-73 (Exhibit 22).

Saal, W., H.J. Glowania, and J. Happ (1991) Pharmacodynamics and pharmacokinetics after subcutaneous and intramuscular injection of human chorionic gonadotropin. *Fertil. Steril.* 56, 225-8 (Exhibit 23).

Sairam, M. R. and P. Manjunath (1982) Studies on pituitary follitropin. XL Induction of hormonal antagonistic activity by chemical deglycosylation. *Mol. Cell Endocrinol.* 28, 139-150 (Exhibit 24).

Sugahara, T., M. R. Pixley, F. Fares, and I. Boime (1996) Characterization of the O-glycosylation sites in the chorionic gonadotropin beta subunit in vivo using site-directed mutagenesis and gene transfer. *J. Biol. Chem.* 271, 20797-20804 (Exhibit 25).

Suganuma, N., M. M. Matzuk, and I. Boime (1989) Elimination of disulfide bonds affects assembly and secretion of the human chorionic gonadotropin beta subunit. *J. Biol. Chem.* 264, 19302-19307 (Exhibit 26).

Van Blerkom, J., M. Antczak, and R. Schrader (1997) The developmental potential of the human oocyte is related to the dissolved oxygen content of follicular fluid: association with vascular endothelial growth factor levels and perifollicular blood flow characteristics. *Hum. Reprod.* 12, 1047-1055 (Exhibit 27); and.

Yen, S. S., O. Llerena, B. Little, and O. H. Pearson (1968) Disappearance rates of endogenous luteinizing hormone and chorioric gonadotropin in man. *J. Clin. Endocrinol. Metab.* 28, 1763-1767 (Exhibit 28).

International Search Report issued Dec. 1, 2003 in connection with PCT International Application No. PCT/US03/02982; and.

Ben-Menahem et al. (2001) The Position of the Alpha and Beta Subunits in a Single Chain Variant of Human Chorionic Gonadotropin Affects the Heterodimeric Interaction of the Subunits and Receptor-Binding Epitope. J. Biol. Chem. 276:29871-879.

* cited by examiner

FIGURE 1

SEQ ID No:1

```
atg aag aca ctc cag ttt ttc ttc ctt ttc tgt tgc tgg aaa gca atc
48
Met Lys Thr Leu Gln Phe Phe Phe Leu Phe Cys Cys Trp Lys Ala Ile
1               5                   10                  15 tgc tgc aat agc tgt gag ctg acc aac atc acc att gca ata gag aaa
96
Cys Cys Asn Ser Cys Glu Leu Thr Asn Ile Thr Ile Ala Ile Glu Lys
            20                  25                  30 gaa gaa tgt cgt ttc tgc ata agc atc aac acc act tgg tgt gct ggc
144
Glu Glu Cys Arg Phe Cys Ile Ser Ile Asn Thr Thr Trp Cys Ala Gly
        35                  40                  45 tac tgc tac acc agg gat ctg gtg tat aag gac cca gcc agg ccc aaa
192
Tyr Cys Tyr Thr Arg Asp Leu Val Tyr Lys Asp Pro Ala Arg Pro Lys
    50                  55                  60 atc cag aaa aca tgt acc ttc aag gaa ctg gta tat gaa aca gtg aga
240
Ile Gln Lys Thr Cys Thr Phe Lys Glu Leu Val Tyr Glu Thr Val Arg
65                  70                  75                  80 gtg ccc ggc tgt gct cac cat gca gat tcc ttg tat aca tac cca gtg
288
Val Pro Gly Cys Ala His His Ala Asp Ser Leu Tyr Thr Tyr Pro Val
            85                  90                  95 gcc acc cag tgt cac tgt ggc aag tgt gac agc gac agc act gat tgt
336
Ala Thr Gln Cys His Cys Gly Lys Cys Asp Ser Asp Ser Thr Asp Cys
                100                 105                 110 act gtg cga ggc ctg ggg ccc agc tac tgc tcc ttt ggt gaa atg aaa
384
Thr Val Arg Gly Leu Gly Pro Ser Tyr Cys Ser Phe Gly Glu Met Lys
        115                 120                 125 gaa gga tcc gga tcg aac gcg acg ggg tca ggt tct aat gca act tca
432
Glu Gly Ser Gly Ser Asn Ala Thr Gly Ser Gly Ser Asn Ala Thr Ser
    130                 135                 140 gga tcc taa
                    441
Gly Ser
145
```

FIGURE 2

SEQ ID No:2

```
atg aag aca ctc cag ttt ttc ttc ctt ttc tgt tgc tgg aaa gca atc
48
Met Lys Thr Leu Gln Phe Phe Phe Leu Phe Cys Cys Trp Lys Ala Ile
1               5                   10                  15 tgc tgc aat agc tgt gag ctg acc aac atc acc att gca ata gag aaa
96
Cys Cys Asn Ser Cys Glu Leu Thr Asn Ile Thr Ile Ala Ile Glu Lys
            20                  25                  30 gaa gaa tgt cgt ttc tgc ata agc atc aac acc act tgg tgt gct ggc
144
Glu Glu Cys Arg Phe Cys Ile Ser Ile Asn Thr Thr Trp Cys Ala Gly
        35                  40                  45 tac tgc tac acc agg gat ctg gtg tat aag gac cca gcc agg ccc aaa
192
Tyr Cys Tyr Thr Arg Asp Leu Val Tyr Lys Asp Pro Ala Arg Pro Lys
    50                  55                  60 atc cag aaa aca tgt acc ttc aag gaa ctg gta tat gaa aca gtg aga
240
Ile Gln Lys Thr Cys Thr Phe Lys Glu Leu Val Tyr Glu Thr Val Arg
65                  70                  75                  80 gtg ccc ggc tgt gct cac cat gca gat tcc ttg tat aca tac cca gtg
288
Val Pro Gly Cys Ala His His Ala Asp Ser Leu Tyr Thr Tyr Pro Val
            85                  90                  95 gcc acc cag tgt cac tgt ggc aag tgt gac agc gac agc act gat tgt
336
Ala Thr Gln Cys His Cys Gly Lys Cys Asp Ser Asp Ser Thr Asp Cys
            100                 105                 110 act gtg cga ggc ctg ggg ccc agc tac tgc tcc ttt ggt gaa atg aaa
384
Thr Val Arg Gly Leu Gly Pro Ser Tyr Cys Ser Phe Gly Glu Met Lys
        115                 120                 125 gaa gga tcc gga tcg aac gcg acg ggg tca ggt tct aat gca act tca
432
Glu Gly Ser Gly Ser Asn Ala Thr Gly Ser Gly Ser Asn Ala Thr Ser
    130                 135                 140 aga tcc gga tcg aac gcg acg ggg tca ggt tct aat gca act tca gga
480
Arg Ser Gly Ser Asn Ala Thr Gly Ser Gly Ser Asn Ala Thr Ser Gly
145                 150                 155                 160 tcc taa
        486
Ser
```

FIGURE 3

SEQ ID No:3

| | | | | | | | | | | | | | | | | |
|---|---|---|---|---|---|---|---|---|---|---|---|---|---|---|---|---|
| atg | aag | aca | ctc | cag | ttt | ttc | ttc | ctt | ttc | tgt | tgc | tgg | aaa | gca | atc | 48 |
| Met | Lys | Thr | Leu | Gln | Phe | Phe | Phe | Leu | Phe | Cys | Cys | Trp | Lys | Ala | Ile | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| tgc | tgc | aat | agc | tgt | gag | ctg | acc | aac | atc | acc | att | gca | ata | gag | aaa | 96 |
| Cys | Cys | Asn | Ser | Cys | Glu | Leu | Thr | Asn | Ile | Thr | Ile | Ala | Ile | Glu | Lys | |
| | | | 20 | | | | | 25 | | | | | 30 | | | |

| | | | | | | | | | | | | | | | | |
|---|---|---|---|---|---|---|---|---|---|---|---|---|---|---|---|---|
| gaa | gaa | tgt | cgt | ttc | tgc | ata | agc | atc | aac | acc | act | tgg | tgt | gct | ggc | 144 |
| Glu | Glu | Cys | Arg | Phe | Cys | Ile | Ser | Ile | Asn | Thr | Thr | Trp | Cys | Ala | Gly | |
| | | 35 | | | | | 40 | | | | | 45 | | | | |

| | | | | | | | | | | | | | | | | |
|---|---|---|---|---|---|---|---|---|---|---|---|---|---|---|---|---|
| tac | tgc | tac | acc | agg | gat | ctg | gtg | tat | aag | gac | cca | gcc | agg | ccc | aaa | 192 |
| Tyr | Cys | Tyr | Thr | Arg | Asp | Leu | Val | Tyr | Lys | Asp | Pro | Ala | Arg | Pro | Lys | |
| | 50 | | | | | 55 | | | | | 60 | | | | | |

| | | | | | | | | | | | | | | | | |
|---|---|---|---|---|---|---|---|---|---|---|---|---|---|---|---|---|
| atc | cag | aaa | aca | tgt | acc | ttc | aag | gaa | ctg | gta | tat | gaa | aca | gtg | aga | 240 |
| Ile | Gln | Lys | Thr | Cys | Thr | Phe | Lys | Glu | Leu | Val | Tyr | Glu | Thr | Val | Arg | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| gtg | ccc | ggc | tgt | gct | cac | cat | gca | gat | tcc | ttg | tat | aca | tac | cca | gtg | 288 |
| Val | Pro | Gly | Cys | Ala | His | His | Ala | Asp | Ser | Leu | Tyr | Thr | Tyr | Pro | Val | |
| | | | | 85 | | | | | 90 | | | | | 95 | | |

| | | | | | | | | | | | | | | | | |
|---|---|---|---|---|---|---|---|---|---|---|---|---|---|---|---|---|
| gcc | acc | cag | tgt | cac | tgt | ggc | aag | tgt | gac | agc | gac | agc | act | gat | tgt | 336 |
| Ala | Thr | Gln | Cys | His | Cys | Gly | Lys | Cys | Asp | Ser | Asp | Ser | Thr | Asp | Cys | |
| | | | | 100 | | | | | 105 | | | | | 110 | | |

| | | | | | | | | | | | | | | | | |
|---|---|---|---|---|---|---|---|---|---|---|---|---|---|---|---|---|
| act | gtg | cga | ggc | ctg | ggg | ccc | agc | tac | tgc | tcc | ttt | ggt | gaa | atg | aaa | 384 |
| Thr | Val | Arg | Gly | Leu | Gly | Pro | Ser | Tyr | Cys | Ser | Phe | Gly | Glu | Met | Lys | |
| | | | 115 | | | | | 120 | | | | | 125 | | | |

| | | | | | | | | | | | | | | | | |
|---|---|---|---|---|---|---|---|---|---|---|---|---|---|---|---|---|
| gaa | gga | tcc | ccc | cgc | ttc | cag | gac | tcc | tct | tcc | tca | aag | gcc | cct | ccc | 432 |
| Glu | Gly | Ser | Pro | Arg | Phe | Gln | Asp | Ser | Ser | Ser | Ser | Lys | Ala | Pro | Pro | |
| | | 130 | | | | | 135 | | | | | 140 | | | | |

| | | | | | | | | | | | | | | | | |
|---|---|---|---|---|---|---|---|---|---|---|---|---|---|---|---|---|
| ccc | agc | ctt | cca | agc | cca | tcc | cga | ctc | ccg | ggg | ccc | tcg | gac | acc | ccg | 480 |
| Pro | Ser | Leu | Pro | Ser | Pro | Ser | Arg | Leu | Pro | Gly | Pro | Ser | Asp | Thr | Pro | |
| 145 | | | | 150 | | | | | 155 | | | | | 160 | | |

| | | | | | | | | | | | | | | | | |
|---|---|---|---|---|---|---|---|---|---|---|---|---|---|---|---|---|
| atc | ctc | cca | caa | act | agt | gct | cct | gat | gtg | cag | gat | tgc | cca | gaa | tgc | 528 |
| Ile | Leu | Pro | Gln | Thr | Ser | Ala | Pro | Asp | Val | Gln | Asp | Cys | Pro | Glu | Cys | |
| | | | | 165 | | | | | 170 | | | | | 175 | | |

| | | | | | | | | | | | | | | | | |
|---|---|---|---|---|---|---|---|---|---|---|---|---|---|---|---|---|
| acg | cta | cag | gaa | aac | cca | ttc | ttc | tcc | cag | ccg | ggt | gcc | cca | ata | ctt | 576 |
| Thr | Leu | Gln | Glu | Asn | Pro | Phe | Phe | Ser | Gln | Pro | Gly | Ala | Pro | Ile | Leu | |
| | | | 180 | | | | | 185 | | | | | 190 | | | |

| | | | | | | | | | | | | | | | | |
|---|---|---|---|---|---|---|---|---|---|---|---|---|---|---|---|---|
| cag | tgc | atg | ggc | tgc | tgc | ttc | tct | aga | gca | tat | ccc | act | cca | cta | agg | 624 |
| Gln | Cys | Met | Gly | Cys | Cys | Phe | Ser | Arg | Ala | Tyr | Pro | Thr | Pro | Leu | Arg | |
| | | 195 | | | | | 200 | | | | | 205 | | | | |

| | | | | | | | | | | | | | | | | |
|---|---|---|---|---|---|---|---|---|---|---|---|---|---|---|---|---|
| tcc | aag | aag | acg | atg | ttg | gtc | caa | aag | aac | gtc | acc | tca | gag | tcc | act | 672 |
| Ser | Lys | Lys | Thr | Met | Leu | Val | Gln | Lys | Asn | Val | Thr | Ser | Glu | Ser | Thr | |
| | 210 | | | | | 215 | | | | | 220 | | | | | |

| | | | | | | | | | | | | | | | | |
|---|---|---|---|---|---|---|---|---|---|---|---|---|---|---|---|---|
| tgc | tgt | gta | gct | aaa | tca | tat | aac | agg | gtc | aca | gta | atg | ggg | ggt | ttc | 720 |
| Cys | Cys | Val | Ala | Lys | Ser | Tyr | Asn | Arg | Val | Thr | Val | Met | Gly | Gly | Phe | |
| 225 | | | | 230 | | | | | 235 | | | | | 240 | | |

| | | | | | | | | | | | | | | | | |
|---|---|---|---|---|---|---|---|---|---|---|---|---|---|---|---|---|
| aaa | gtg | gag | aac | cac | acg | gcg | tgc | cac | tgc | agt | act | tgt | tat | tat | cac | 768 |
| Lys | Val | Glu | Asn | His | Thr | Ala | Cys | His | Cys | Ser | Thr | Cys | Tyr | Tyr | His | |
| | | | | 245 | | | | | 250 | | | | | 255 | | |

| | | | | | |
|---|---|---|---|---|---|
| aaa | tct | taa | | | 777 |
| Lys | Ser | | | | |

FIGURE 4

SEQ ID No:4

```
atg aag aca ctc cag ttt ttc ttc ctt ttc tgt tgc tgg aaa gca atc
48
Met Lys Thr Leu Gln Phe Phe Phe Leu Phe Cys Cys Trp Lys Ala Ile
1               5                   10                  15 tgc tgc aat agc tgt gag ctg acc aac atc acc att gca ata gag aaa
96
Cys Cys Asn Ser Cys Glu Leu Thr Asn Ile Thr Ile Ala Ile Glu Lys
            20                  25                  30 gaa gaa tgt cgt ttc tgc ata agc atc aac acc act tgg tgt gct ggc
144
Glu Glu Cys Arg Phe Cys Ile Ser Ile Asn Thr Thr Trp Cys Ala Gly
        35                  40                  45 tac tgc tac acc agg gat ctg gtg tat aag gac cca gcc agg ccc aaa
192
Tyr Cys Tyr Thr Arg Asp Leu Val Tyr Lys Asp Pro Ala Arg Pro Lys
    50                  55                  60 atc cag aaa aca tgt acc ttc aag gaa ctg gta tat gaa aca gtg aga
240
Ile Gln Lys Thr Cys Thr Phe Lys Glu Leu Val Tyr Glu Thr Val Arg
65                  70                  75                  80 gtg ccc ggc tgt gct cac cat gca gat tcc ttg tat aca tac cca gtg
288
Val Pro Gly Cys Ala His His Ala Asp Ser Leu Tyr Thr Tyr Pro Val
            85                  90                  95 gcc acc cag tgt cac tgt ggc aag tgt gac agc gac agc act gat tgt
336
Ala Thr Gln Cys His Cys Gly Lys Cys Asp Ser Asp Ser Thr Asp Cys
        100                 105                 110 act gtg cga ggc ctg ggg ccc agc tac tgc tcc ttt ggt gaa atg aaa
384
Thr Val Arg Gly Leu Gly Pro Ser Tyr Cys Ser Phe Gly Glu Met Lys
    115                 120                 125 gaa gga tcc gga tcg aac gcg acg ggg tca ggt tct aat gca act tca
432
Glu Gly Ser Gly Ser Asn Ala Thr Gly Ser Gly Ser Asn Ala Thr Ser
130                 135                 140 gga tcc act agt gct cct gat gtg cag gat tgc cca gaa tgc acg cta
480
Gly Ser Thr Ser Ala Pro Asp Val Gln Asp Cys Pro Glu Cys Thr Leu
145                 150                 155                 160 cag gaa aac cca ttc ttc tcc cag ccg ggt gcc cca ata ctt cag tgc
528
Gln Glu Asn Pro Phe Phe Ser Gln Pro Gly Ala Pro Ile Leu Gln Cys
            165                 170                 175 atg ggc tgc tgc ttc tct aga gca tat ccc act cca cta agg tcc aag
576
Met Gly Cys Cys Phe Ser Arg Ala Tyr Pro Thr Pro Leu Arg Ser Lys
        180                 185                 190 aag acg atg ttg gtc caa aag aac gtc acc tca gag tcc act tgc tgt
624
Lys Thr Met Leu Val Gln Lys Asn Val Thr Ser Glu Ser Thr Cys Cys
    195                 200                 205 gta gct aaa tca tat aac agg gtc aca gta atg ggg ggt ttc aaa gtg
672
Val Ala Lys Ser Tyr Asn Arg Val Thr Val Met Gly Gly Phe Lys Val
    210                 215                 220 gag aac cac acg gcg tgc cac tgc agt act tgt tat tat cac aaa tct
720
Glu Asn His Thr Ala Cys His Cys Ser Thr Cys Tyr Tyr His Lys Ser
225                 230                 235                 240 taa
723
```

FIGURE 5

SEQ ID No:5

```
atg aag aca ctc cag ttt ttc ttc ctt ttc tgt tgc tgg aaa gca atc
Met Lys Thr Leu Gln Phe Phe Phe Leu Phe Cys Cys Trp Lys Ala Ile
1               5                   10                  15 tgc tgc aat agc tgt gag ctg acc aac atc acc att gca ata gag aaa
Cys Cys Asn Ser Cys Glu Leu Thr Asn Ile Thr Ile Ala Ile Glu Lys
            20                  25                  30 gaa gaa tgt cgt ttc tgc ata agc atc aac acc act tgg tgt gct ggc
Glu Glu Cys Arg Phe Cys Ile Ser Ile Asn Thr Thr Trp Cys Ala Gly
        35                  40                  45 tac tgc tac acc agg gat ctg gtg tat aag gac cca gcc agg ccc aaa
Tyr Cys Tyr Thr Arg Asp Leu Val Tyr Lys Asp Pro Ala Arg Pro Lys
    50                  55                  60 atc cag aaa aca tgt acc ttc aag gaa ctg gta tat gaa aca gtg aga
Ile Gln Lys Thr Cys Thr Phe Lys Glu Leu Val Tyr Glu Thr Val Arg
65                  70                  75                  80 gtg ccc ggc tgt gct cac cat gca gat tcc ttg tat aca tac cca gtg
Val Pro Gly Cys Ala His His Ala Asp Ser Leu Tyr Thr Tyr Pro Val
            85                  90                  95 gcc acc cag tgt cac tgt ggc aag tgt gac agc gac agc act gat tgt
Ala Thr Gln Cys His Cys Gly Lys Cys Asp Ser Asp Ser Thr Asp Cys
            100                 105                 110 act gtg cga ggc ctg ggg ccc agc tac tgc tcc ttt ggt gaa atg aaa
Thr Val Arg Gly Leu Gly Pro Ser Tyr Cys Ser Phe Gly Glu Met Lys
        115                 120                 125 gaa gga tcc gga tcg aac gcg acg ggg tca ggt tct aat gca act tca
Glu Gly Ser Gly Ser Asn Ala Thr Gly Ser Gly Ser Asn Ala Thr Ser
    130                 135                 140 aga tcc gga tcg aac gcg acg ggg tca ggt tct aat gca act tca gga
Arg Ser Gly Ser Asn Ala Thr Gly Ser Gly Ser Asn Ala Thr Ser Gly
145                 150                 155                 160 tcc act agt gct cct gat gtg cag gat tgc cca gaa tgc acg cta cag
Ser Thr Ser Ala Pro Asp Val Gln Asp Cys Pro Glu Cys Thr Leu Gln
            165                 170                 175 gaa aac cca ttc ttc tcc cag ccg ggt gcc cca ata ctt cag tgc atg
Glu Asn Pro Phe Phe Ser Gln Pro Gly Ala Pro Ile Leu Gln Cys Met
        180                 185                 190 ggc tgc tgc ttc tct aga gca tat ccc act cca cta agg tcc aag aag
Gly Cys Cys Phe Ser Arg Ala Tyr Pro Thr Pro Leu Arg Ser Lys Lys
    195                 200                 205 acg atg ttg gtc caa aag aac gtc acc tca gag tcc act tgc tgt gta
Thr Met Leu Val Gln Lys Asn Val Thr Ser Glu Ser Thr Cys Cys Val
210                 215                 220 gct aaa tca tat aac agg gtc aca gta atg ggg ggt ttc aaa gtg gag
Ala Lys Ser Tyr Asn Arg Val Thr Val Met Gly Gly Phe Lys Val Glu
```

FIGURE 6
A) 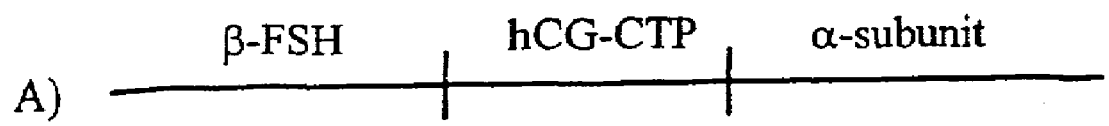
B) 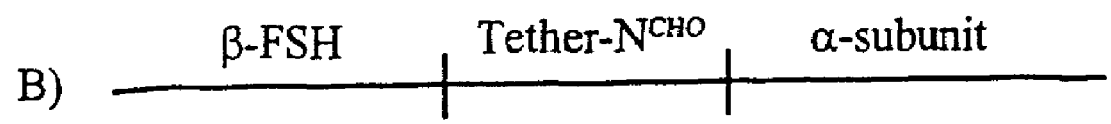

FIGURE 12

Table I: Pharmacokinetic parameter estimates after IV bolus injection of r-hFSH-CTP and r-hFSH at a dose of 10 IU/kg

| PARAMETER | r-hFSH-CTP | r-hFSH |
|---|---|---|
| $T_{1/2\ alpha\ (distribution)}$ (hr) | 3.16 | 1.39 |
| $T_{1/2\ beta\ (elimination)}$ (hr) | 35.29 | 8.25 |
| AUC (mIU/ml·d) | 278[a] | 38.8 |
| Clearance (l/kg·hr) | 1.50[b] | 10.74 |

[a] see discussion
[b] see discussion

FIGURE 13

Table II: Mean pharmacokinetic parameter estimates after subcutaneous injection of r-hFSH-CTP and r-hFSH at a dose of 10 IU/kg.

| PARAMETER | r-hFSH-CTP (n=4) | r-hFSH (n=2) |
|---|---|---|
| $T_{1/2\ elimination}$ (hrs) | 35.23 | 15.74 |
| $T_{1/2\ absorption}$ (hrs) | 5.04 | 1.75 |
| $C_{max}$ (mIU/ml) | 101.26[a] | 25.77 |
| $T_{max}$ (hours) | 16.39 | 5.95 |
| AUC (mIU/ml·d) | 275.31[a] | 30.96 |
| Bioavailability (%) (AUCsc/AUCiv) | 99 | 80 |

[a] see discussion

FIGURE 14

SEQ ID No:6

Beta hCG

```
  1                            10           CHO
Ser-Lys-Glu-Pro-Leu-Arg-Pro-Arg-Cys-Arg-Pro-Ile-Asn-Ala-Thr-Leu-Ala-
            20                           CHO
Val-Glu-Lys-Glu-Gly-Cys-Pro-Val-Cys-Ile-Thr-Val-Asn-Thr-Thr-Ile-Cys-
                        40                              50
Ala-Gly-Tyr-Cys-Pro-Thr-Met-Thr-Arg-Val-Leu-Gln-Gly-Val-Leu-Pro-Ala-
                            60
Leu-Pro-Gln-Val-Val-Cys-Asn-Tyr-Arg-Asp-Val-Arg-Phe-Glu-Ser-Ile-Arg-
        70                              80
Leu-Pro-Gly-Cys-Pro-Arg-Gly-Val-Asn-Pro-Val-Val-Ser-Tyr-Ala-Val-Ala-
                    90                                  100
Leu-Ser-Cys-Gln-Cys-Ala-Leu-Cys-Arg-Arg-Ser-Thr-Thr-Asp-Cys-Gly-Gly-
                        110
Pro-Lys-Asp-His-Pro-Leu-Thr-Cys-Asp-Asp-Pro-Arg-Phe-Gln-Asp-Ser-Ser-
 120  CHO                      CHO         130      CHO
Ser-Ser-Lys-Ala-Pro-Pro-Pro-Ser-Leu-Pro-Ser-Pro-Ser-Arg-Leu-Pro-Gly-
    CHO   140                 145
Pro-Ser-Asp-Thr-Pro-Ile-Leu-Pro-Gln
```

FIGURE 15
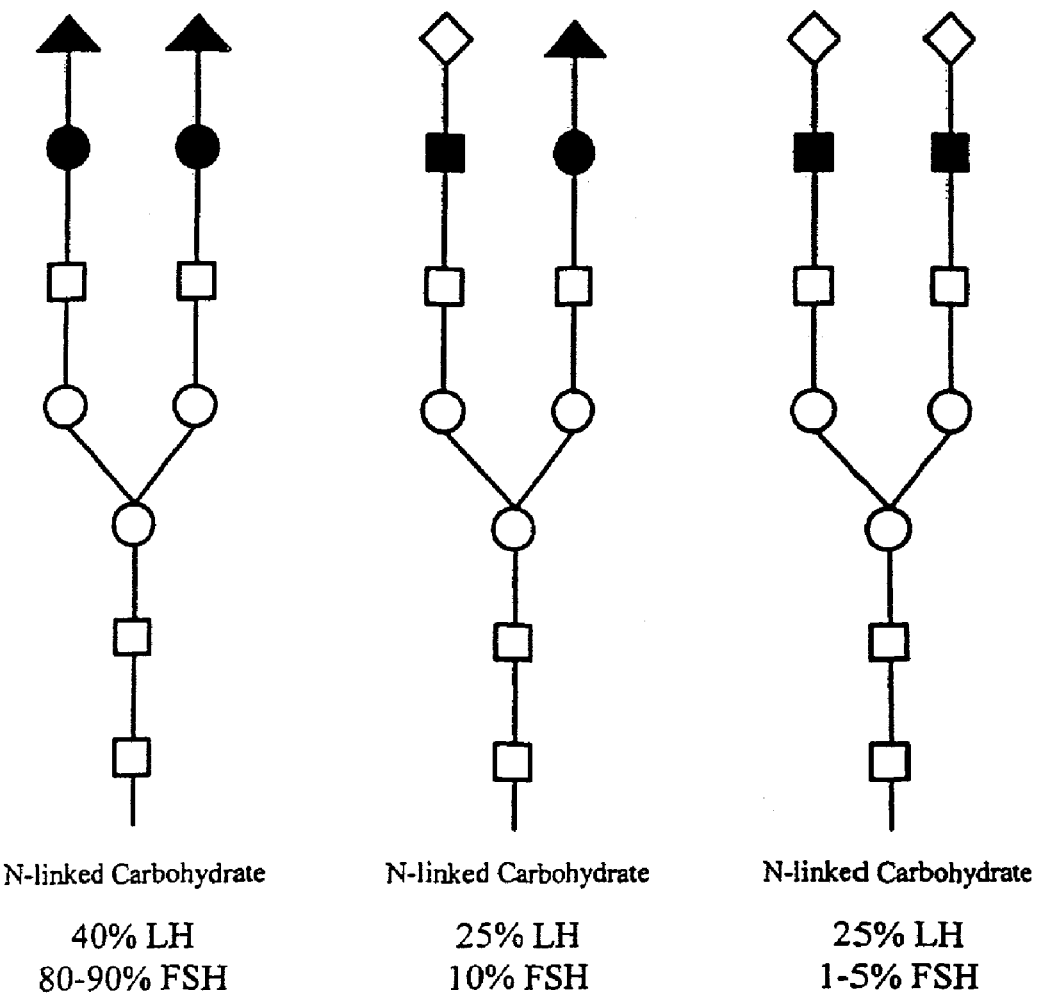
N-linked Carbohydrate
40% LH
80-90% FSH
N-linked Carbohydrate
25% LH
10% FSH
N-linked Carbohydrate
25% LH
1-5% FSH
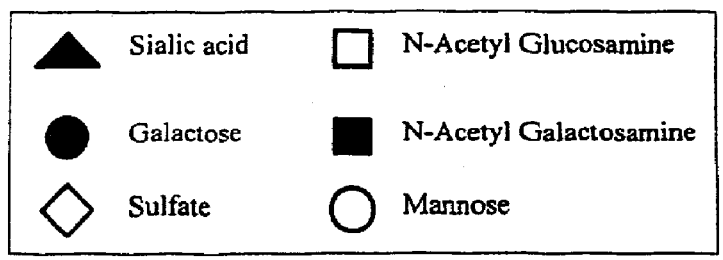

FIGURE 17

SEQ ID No:7

```
      M    K    T    L    Q    F    F    F    L    F    C    C    W
  1   atg  aag  aca  ctc  cag  ttt  ttc  ttc  ctt  ttc  tgt  tgc  tgg   39

K    A    I    C    C    N    S    C    E    L    T    N    I
 40   aaa  gca  atc  tgc  tgc  aat  agc  tgt  gag  ctg  acc  aac  atc   78

T    I    A    I    E    K    E    E    C    R    F    C    I
 79   acc  att  gca  ata  gag  aaa  gaa  gaa  tgt  cgt  ttc  tgc  ata   117

S    I    N    T    T    W    C    A    G    Y    C    Y    T
118   agc  atc  aac  acc  act  tgg  tgt  gct  ggc  tac  tgc  tac  acc   156

R    D    L    V    Y    K    D    P    A    R    P    K    I
157   agg  gat  ctg  gtg  tat  aag  gac  cca  gcc  agg  ccc  aaa  atc   195

Q    K    T    C    T    F    K    E    L    V    Y    E    T
196   cag  aaa  aca  tgt  acc  ttc  aag  gaa  ctg  gta  tat  gaa  aca   234

V    R    V    P    G    C    A    H    H    A    D    S    L
235   gtg  aga  gtg  ccc  ggc  tgt  gct  cac  cat  gca  gat  tcc  ttg   273

Y    T    Y    P    V    A    T    Q    C    H    C    G    K
274   tat  aca  tac  cca  gtg  gcc  acc  cag  tgt  cac  tgt  ggc  aag   312

C    D    S    D    S    T    D    C    T    V    R    G    L
313   tgt  gac  agc  gac  agc  act  gat  tgt  act  gtg  cga  ggc  ctg   351

G    P    S    Y    C    S    F    G    E    M    K    E    *
352   ggg  ccc  agc  tac  tgc  tcc  ttt  ggt  gaa  atg  aaa  gaa  taa   390
```

FIGURE 18

SEQ ID No:8

```
     M   D   Y   Y   R   K   Y   A   A   I   F   L   V
  1  atg gat tac tac aga aaa tat gca gct atc ttt ctg gtc   39

T   L   S   V   F   L   H   V   L   H   S   A   P
 40  aca ttg tcg gtg ttt ctg cat gtt ctc cat tcc gct cct   78

D   V   Q   D   C   P   E   C   T   L   Q   E   N
 79  gat gtg cag gat tgc cca gaa tgc acg cta cag gaa aac  117

P   F   F   S   Q   P   G   A   P   I   L   Q   C
118  cca ttc ttc tcc cag ccg ggt gcc cca ata ctt cag tgc  156

M   G   C   C   F   S   R   A   Y   P   T   P   L
157  atg ggc tgc tgc ttc tct aga gca tat ccc act cca cta  195

R   S   K   K   T   M   L   V   Q   K   N   V   T
196  agg tcc aag aag acg atg ttg gtc caa aag aac gtc acc  234

S   E   S   T   C   C   V   A   K   S   Y   N   R
235  tca gag tcc act tgc tgt gta gct aaa tca tat aac agg  273

V   T   V   M   G   G   F   K   V   E   N   H   T
274  gtc aca gta atg ggg ggt ttc aaa gtg gag aac cac acg  312

A   C   H   C   S   T   C   Y   Y   H   K   S   *
313  gcg tgc cac tgc agt act tgt tat tat cac aaa tct taa  351
```

FIGURE 21

| Table 3: Mean PK parameters (n=3) of serum hFSH after IV injections of hFSH, FSH-CTP and N2 in the dose of 2800 ng/rat to immature female rats (21 days old). | | | |
|---|---|---|---|
| *Parameters | hFSH | FSH-CTP | N-2 |
| $AUC_{0-infinity}$ (ng/h/ml) | 1491 | 3887 | 4802 |
| t1/2(Beta phase)(h) | 3.7 | 7.1 | 7.3 |

SEQUENCE LISTING

<160> NUMBER OF SEQ ID NOS: 9

<210> SEQ ID NO 1
<211> LENGTH: 441
<212> TYPE: DNA
<213> ORGANISM: human
<220> FEATURE:
<221> NAME/KEY: misc_feature
<223> OTHER INFORMATION: hFSHb-N2

<400> SEQUENCE: 1

| | | | | | |
|---|---|---|---|---|---|
| atgaagacac | tccagttttt | cttccttttc | tgttgctgga | aagcaatctg | ctgcaatagc | 60 |
| tgtgagctga | ccaacatcac | cattgcaata | gagaaagaag | aatgtcgttt | ctgcataagc | 120 |
| atcaacacca | cttggtgtgc | tggctactgc | tacaccaggg | atctggtgta | taaggaccca | 180 |
| gccaggccca | aaatccagaa | aacatgtacc | ttcaaggaac | tggtatatga | aacagtgaga | 240 |
| gtgcccggct | gtgctcacca | tgcagattcc | ttgtatacat | acccagtggc | cacccagtgt | 300 |
| cactgtggca | agtgtgacag | cgacagcact | gattgtactg | tgcgaggcct | ggggcccagc | 360 |
| tactgctcct | ttggtgaaat | gaaagaagga | tccggatcga | acgcgacggg | gtcaggttct | 420 |
| aatgcaactt | caggatccta | a | | | | 441 |

<210> SEQ ID NO 2
<211> LENGTH: 486
<212> TYPE: DNA
<213> ORGANISM: human
<220> FEATURE:
<221> NAME/KEY: misc_feature
<223> OTHER INFORMATION: hFSHb-N4

<400> SEQUENCE: 2

| | | | | | |
|---|---|---|---|---|---|
| atgaagacac | tccagttttt | cttccttttc | tgttgctgga | aagcaatctg | ctgcaatagc | 60 |
| tgtgagctga | ccaacatcac | cattgcaata | gagaaagaag | aatgtcgttt | ctgcataagc | 120 |
| atcaacacca | cttggtgtgc | tggctactgc | tacaccaggg | atctggtgta | taaggaccca | 180 |
| gccaggccca | aaatccagaa | aacatgtacc | ttcaaggaac | tggtatatga | aacagtgaga | 240 |
| gtgcccggct | gtgctcacca | tgcagattcc | ttgtatacat | acccagtggc | cacccagtgt | 300 |
| cactgtggca | agtgtgacag | cgacagcact | gattgtactg | tgcgaggcct | ggggcccagc | 360 |
| tactgctcct | ttggtgaaat | gaaagaagga | tccggatcga | acgcgacggg | gtcaggttct | 420 |
| aatgcaactt | caagatccgg | atcgaacgcg | acggggtcag | gttctaatgc | aacttcagga | 480 |
| tcctaa | | | | | | 486 |

<210> SEQ ID NO 3
<211> LENGTH: 777
<212> TYPE: DNA
<213> ORGANISM: human
<220> FEATURE:
<221> NAME/KEY: misc_feature
<223> OTHER INFORMATION: hFSHb-CTP-alpha

<400> SEQUENCE: 3

| | | | | | |
|---|---|---|---|---|---|
| atgaagacac | tccagttttt | cttccttttc | tgttgctgga | aagcaatctg | ctgcaatagc | 60 |
| tgtgagctga | ccaacatcac | cattgcaata | gagaaagaag | aatgtcgttt | ctgcataagc | 120 |
| atcaacacca | cttggtgtgc | tggctactgc | tacaccaggg | atctggtgta | taaggaccca | 180 |
| gccaggccca | aaatccagaa | aacatgtacc | ttcaaggaac | tggtatatga | aacagtgaga | 240 |

-continued

```
gtgcccggct gtgctcacca tgcagattcc ttgtatacat acccagtggc cacccagtgt    300
cactgtggca agtgtgacag cgacagcact gattgtactg tgcgaggcct ggggcccagc    360
tactgctcct ttggtgaaat gaaagaagga tccccccgct ccaggactc ctcttcctca     420 aaggccccte cccccagcct tccaagccca tcccgactcc cggggccctc ggacaccccg    480
atcctcccac aaactagtgc tcctgatgtg caggattgcc cagaatgcac gctacaggaa    540
aacccattct tctcccagcc gggtgcccca atacttcagt gcatgggctg ctgcttctct    600
agagcatatc ccactccact aaggtccaag aagacgatgt tggtccaaaa gaacgtcacc    660
tcagagtcca cttgctgtgt agctaaatca tataacaggg tcacagtaat gggggggtttc  720 aaagtggaga accacacggc gtgccactgc agtacttgtt attatcacaa atcttaa      777
```

<210> SEQ ID NO 4
<211> LENGTH: 723
<212> TYPE: DNA
<213> ORGANISM: human
<220> FEATURE:
<221> NAME/KEY: misc_feature
<223> OTHER INFORMATION: hFSH-N2-alpha

<400> SEQUENCE: 4

```
atgaagacac tccagttttt cttccttttc tgttgctgga aagcaatctg ctgcaatagc    60
tgtgagctga ccaacatcac cattgcaata gagaaagaag aatgtcgttt ctgcataagc    120
atcaacacca cttggtgtgc tggctactgc tacaccaggg atctggtgta taaggaccca    180
gccaggccca aaatccagaa acatgtacc ttcaaggaac tggtatatga acagtgaga     240 gtgcccggct gtgctcacca tgcagattcc ttgtatacat acccagtggc cacccagtgt    300
cactgtggca agtgtgacag cgacagcact gattgtactg tgcgaggcct ggggcccagc    360
tactgctcct ttggtgaaat gaaagaagga tccggatcga acgcgacggg gtcaggttct    420
aatgcaactt caggatccac tagtgctcct gatgtgcagg attgcccaga atgcacgcta    480
caggaaaacc cattcttctc ccagccgggt gccccaatac ttcagtgcat gggctgctgc    540
ttctctagag catatcccac tccactaagg tccaagaaga cgatgttggt ccaaaagaac    600
gtcacctcag agtccacttg ctgtgtagct aaatcatata cagggtcac agtaatgggg    660 ggtttcaaag tggagaacca cacggcgtgc cactgcagta cttgttatta tcacaaatct    720
taa                                                                 723
```

<210> SEQ ID NO 5
<211> LENGTH: 768
<212> TYPE: DNA
<213> ORGANISM: human
<220> FEATURE:
<221> NAME/KEY: misc_feature
<223> OTHER INFORMATION: hFSH-N4-alpha

<400> SEQUENCE: 5

```
atgaagacac tccagttttt cttccttttc tgttgctgga aagcaatctg ctgcaatagc    60
tgtgagctga ccaacatcac cattgcaata gagaaagaag aatgtcgttt ctgcataagc    120
atcaacacca cttggtgtgc tggctactgc tacaccaggg atctggtgta taaggaccca    180
gccaggccca aaatccagaa acatgtacc ttcaaggaac tggtatatga acagtgaga     240 gtgcccggct gtgctcacca tgcagattcc ttgtatacat acccagtggc cacccagtgt    300
cactgtggca agtgtgacag cgacagcact gattgtactg tgcgaggcct ggggcccagc    360
tactgctcct ttggtgaaat gaaagaagga tccggatcga acgcgacggg gtcaggttct    420
```

```
aatgcaactt caagatccgg atcgaacgcg acggggtcag gttctaatgc aacttcagga    480
tccactagtg ctcctgatgt gcaggattgc ccagaatgca cgctacagga aacccattc    540 ttctcccagc cgggtgcccc aatacttcag tgcatgggct gctgcttctc tagagcatat    600
cccactccac taaggtccaa gaagacgatg ttggtccaaa gaacgtcac ctcagagtcc    660 acttgctgtg tagctaaatc atataacagg gtcacagtaa tggggggttt caaagtggag    720
aaccacacgg cgtgccactg cagtacttgt tattatcaca aatcttaa    768
```

```
<210> SEQ ID NO 6
<211> LENGTH: 145
<212> TYPE: PRT
<213> ORGANISM: human
<220> FEATURE:
<221> NAME/KEY: misc_feature
<223> OTHER INFORMATION: beta-hCG

<400> SEQUENCE: 6

Ser Lys Glu Pro Leu Arg Pro Arg Cys Arg Pro Ile Asn Ala Thr Leu
 1               5                  10                  15

Ala Val Glu Lys Glu Gly Cys Pro Val Cys Ile Thr Val Asn Thr Thr
            20                  25                  30

Ile Cys Ala Gly Tyr Cys Pro Thr Met Thr Arg Val Leu Gln Gly Val
        35                  40                  45

Leu Pro Ala Leu Pro Gln Val Val Cys Asn Tyr Arg Asp Val Arg Phe
    50                  55                  60

Glu Ser Ile Arg Leu Pro Gly Cys Pro Arg Gly Val Asn Pro Val Val
65                  70                  75                  80

Ser Tyr Ala Val Ala Leu Ser Cys Gln Cys Ala Leu Cys Arg Arg Ser
                85                  90                  95

Thr Thr Asp Cys Gly Gly Pro Lys Asp His Pro Leu Thr Cys Asp Asp
            100                 105                 110

Pro Arg Phe Gln Asp Ser Ser Ser Lys Ala Pro Pro Pro Ser Leu
        115                 120                 125

Pro Ser Pro Ser Arg Leu Pro Gly Pro Ser Asp Thr Pro Ile Leu Pro
    130                 135                 140

Gln
145
```

```
<210> SEQ ID NO 7
<211> LENGTH: 390
<212> TYPE: DNA
<213> ORGANISM: human
<220> FEATURE:
<221> NAME/KEY: misc_feature
<223> OTHER INFORMATION: beta-hFSH

<400> SEQUENCE: 7
atgaagacac tccagttttt cttccttttc tgttgctgga agcaatctg ctgcaatagc    60 tgtgagctga ccaacatcac cattgcaata gagaaagaag aatgtcgttt ctgcataagc    120
atcaacacca cttggtgtgc tggctactgc tacaccaggg atctggtgta taggaccca    180 gccaggccca aaatccagaa acatgtacc ttcaaggaac tggtatatga acagtgaga    240 gtgcccggct gtgctcacca tgcagattcc ttgtatacat acccagtggc cacccagtgt    300
cactgtggca agtgtgacag cgacagcact gattgtactg tgcgaggcct ggggcccagc    360
tactgttcct ttggtgaaat gaaagaataa    390
```

```
<210> SEQ ID NO 8
<211> LENGTH: 351
<212> TYPE: DNA
<213> ORGANISM: human
<220> FEATURE:
<221> NAME/KEY: misc_feature
<223> OTHER INFORMATION: alpha-hFSH

<400> SEQUENCE: 8
atggattact acagaaaata tgcagctatc tttctggtca cattgtcggt gtttctgcat       60
gttctccatt ccgctcctga tgtgcaggat tgcccagaat gcacgctaca ggaaaaccca      120
ttcttctccc agccgggtgc cccaatactt cagtgcatgg gctgctgctt ctctagagca      180
tatcccactc cactaaggtc caagaagacg atgttggtcc aaaagaacgt caccctcagag     240 tccacttgct gtgtagctaa atcatataac agggtcacag taatgggggg tttcaaagtg      300
gagaaccaca cggcgtgcca ctgcagtact tgttattatc acaaatctta a               351

<210> SEQ ID NO 9
<211> LENGTH: 16
<212> TYPE: PRT
<213> ORGANISM: human

<400> SEQUENCE: 9

Ser Gly Ser Asn Ala Thr Gly Ser Gly Ser Asn Ala Thr Ser Gly Ser
1               5                   10                  15
```

LONG-ACTING FOLLICLE STIMULATING HORMONE ANALOGUES AND USES THEREOF

This application is a continuation-in-part of U.S. Ser. No. 10/062,910, filed Jan. 31, 2002 now abandoned, the content of which is hereby incorporated into this application by reference.

The invention described herein was made with government support under grant number DK-51266 from the National Institutes of Health. Accordingly, the United States government has certain rights in this invention.

Throughout this application, various publications are referenced by author and publication date. Full citations for these publications may be found at the end of the specification immediately preceding the claims. The disclosure of these publications is hereby incorporated by reference into this application to describe more fully the art to which this invention pertains.

BACKGROUND OF THE INVENTION

The pituitary glycoprotein hormone, follicle stimulating hormone (FSH), is a heterodimer comprised of two non-covalently bound subunits, α and β (Pierce et al, 1981). The α-subunit is interchangeable among the hormones of this family, which include luteinizing hormone (LH), thyrotropin stimulating hormone (TSH) and chorionic gonadotropin (CG), in addition to FSH. The β-subunit, on the other hand, is unique to each hormone and is primarily responsible for the biological specificity of hormone action (see FIGS. 17 and 18 for the sequences of the hFSH α and β subunits, respectively).

Human FSH (hFSH) contains four N-linked carbohydrate moieties, two on each of the α- and β-subunits. A schematic of the carbohydrate moieties on hLH and hFSH is shown in FIG. 15. While the functional significance of these moieties is poorly understood, they are likely to be important for proper protein folding, subunit assembly and secretion of the hormone (Suganuma et al 1989; Feng et al, 1995). The carbohydrate moieties may also be obligatory for signal transduction, although partially deglycosylated hormones show preserved receptor binding (Calvo et al, 1986; Sairam et al, 1982).

Among the glycoprotein hormones, hCG is known to have the longest circulating half-life. This has been attributed to the presence of four O-linked glycosylation sites on the carboxyterminal peptide (CTP) sequence of the β-subunit, corresponding to amino acids 113–145 (Matzuk et al, 1990). In contrast with N-linked sugars, deglycosylation of O-linked moieties does not affect signal transduction, and hCG devoid of this extension maintains its in vitro bioactivity. Schematic examples of N-linked and O-linked carbohydrates are shown in FIG. 16.

Instead, the importance of the O-linked sugars lies in providing enhanced stability of the hormone in vivo. This was initially deduced from comparisons between hCG and hLH, whose biological activity and β subunits are remarkably similar but whose serum half lives are dramatically different. The β subunits of hCG and hLH share greater than 85% sequence identity through the N-terminal 113 amino acids (Pierce et al, 1981). In addition, these two hormones share a common receptor and elicit similar biologic activity following receptor binding. However, the serum half-life of hCG is almost five-times that of hLH (Porchet et al, 1995; Saal et al, 1991; Yen et al, 1968). The primary structural difference between β-hCG and β-hLH is the additional carboxy-terminal amino acids comprising the CTP sequence of β-hCG. This carboxy-terminal peptide, specifically its O-linked glycosylation sequences, is thus likely to be responsible for both the decreased metabolism and excretion of hCG, and thus also for its notably increased serum half-life over the relatively transient hLH.

The importance of the CTP in promoting hormone stability was demonstrated by the construction of a fusion protein consisting of the CTP portion of the β-subunit of hCG and the carboxy terminus of β-hFSH. This β-hFSH-CTP fusion produced a long-acting hFSH agonist which was able to dimerize with a coexpressed α-subunit to produce a functional FSH hormone (Fares et al, 1992). Importantly, this β-hFSH-CTP demonstrated similar in vitro bioactivity and substantially increased in vivo bioactivity compared with preparations of native hFSH.

Thus, merely adding the CTP sequence to β-hFSH was sufficient to increase the biological activity of the hormone, most likely through an increase in serum-half life. Indeed, recent pharmacokinetic parameter estimates in humans have demonstrated that this β-hFSH-CTP analog has an elimination half-life of 2 to 3 times longer than that of native recombinant hFSH (Bouloux et al, 2001).

Current pharmacologic formulations of FSH include purified urinary derivatives and, more recently, recombinant human FSH (r-hFSH). Due to its relatively short half-life, hFSH must be administered as a daily intramuscular or subcutaneous injection, often for 8 to 12 days when used for ovulation induction (LeContonnec et al, 1994). These regimens of controlled ovarian hyperstimulation are associated with a number of side effects, including local irritation and discomfort, which result in poor compliance and a reduction in therapeutic efficacy.

A long-acting FSH formulation requiring less frequent administration would provide an important development for subjects requiring gonadotropin replacement therapy.

The present invention is based on the surprising and unexpected finding that the addition of multiple N-linked glycosylation sequences confers increased protein stability, as demonstrated by an increased in vivo serum half-life. Importantly, the addition of these novel N-linked moieties does not alter the biological activity of the hFSH analogues disclosed herein, as might have been expected given the known importance of N-linked sugars in signal transduction initiated by gonadotropin hormones. Thus, the present invention provides novel hFSH analogues that have an increased serum half-life without sacrificing biological activity, offering a significant advantage over current technologies in gonadotropin replacement therapy. Such therapies are important for the treatment of infertility and have particular relevance to increasing the efficacy of in vitro fertilization protocols, both in agriculturally important mammals and in humans.

SUMMARY OF THE INVENTION

This invention provides a synthetic FSH comprising a β-FSH subunit, an α-FSH subunit and a half-life-increasing moiety, wherein the β-FSH subunit, α-FSH subunit and half-life-increasing moiety are covalently bound.

This invention also provides a synthetic FSH comprising a β-FSH subunit covalently bound to a polypeptide segment comprising the amino acid sequence ser-gly-ser-asn-ala-thr-gly-ser-gly-ser-asn-ala-thr-ser-gly-ser. (SEQ ID NO:9).

This invention also provides a synthetic FSH comprising a β-FSH subunit, an α-FSH subunit and a polypeptide segment comprising the amino acid sequence ser-gly-serasn-ala-thr-gly-ser-gly-ser-asn-ala-thr-ser-gly-ser, (SEQ ID NO:9), wherein the β-FSH subunit, α-FSH subunit and polypeptide segment are covalently bound.

This invention also provides a pharmaceutical composition comprising a synthetic FSH of the instant invention and a pharmaceutically acceptable carrier.

This invention further provides an article of manufacture comprising (a) the instant pharmaceutical composition, and (b) a label and/or instructions indicating a use of the pharmaceutical composition for the enhancement of fertility, egg production and/or spermatogenesis.

This invention provides nucleic acids encoding the instant synthetic FSH polypeptides, as well as expression vectors and suitable host cells for expressing these polypeptides.

This invention also provides a method for producing the polypeptides of the instant invention that comprises growing a suitable host cell transfected with a vector encoding the polypeptide under conditions permitting its expression and recovering the polypeptide so expressed.

This invention additionally provides a method for producing a synthetic FSH, which comprises co-expressing (i) a nucleic acid which encodes an α-FSH subunit, and (ii) a nucleic acid which encodes a polypeptide comprising a β-FSH subunit and a polypeptide segment comprising the amino acid sequence ser-gly-ser-asn-ala-thr-gly-ser-gly-ser-asn-ala-thr-ser-gly-ser, (SEQ ID NO:9), under conditions permitting such co-expression; and recovering the synthetic FSH so produced.

This invention provides a method for increasing a subject's fertility which comprises administering to the subject an amount of the instant synthetic FSH effective to enhance the subject's fertility.

This invention also provides a method for increasing a subject's spermatogenesis which comprises administering to the subject an amount of the instant synthetic FSH effective to enhance the subject's spermatogenesis.

This invention also provides a method for increasing a subject's egg production which comprises administering to the subject an amount of the instant synthetic FSH effective to enhance the subject's egg production.

Finally, this invention provides a method of increasing the half-life of a molecule in a subject, which method comprises glycosylating the molecule in a manner effective to increase the molecule's half-life.

BRIEF DESCRIPTION OF THE FIGURES

FIG. 1: Nucleotide and predicted amino acid sequence of the fusion protein β-hFSH-N2 (SEQ ID NO:1). The N2 sequence is amino acids 130 through 146.

FIG. 2: Nucleotide and predicted amino acid sequence of the fusion protein β-hFSH-N4 (SEQ ID NO:2). The N4 sequence is amino acids 130 through 161.

FIG. 3: Nucleotide and predicted amino acid sequence of the fusion protein β-hFSH-CTP-α-hFSH. (SEQ ID NO:3)

FIG. 4: Nucleotide and predicted amino acid sequence of the fusion protein β-hFSH-N2-α-hFSH (SEQ ID NO:4).

FIG. 5: Nucleotide and predicted amino acid sequence of the fusion protein β-hFSH-N4-α-hFSH (SEQ ID NO:5).

FIG. 6: (Panel A) Schematic β-hFSH-CTP-α construct; (Panel B) Schematic β-hFSH-N2/N4-α construct.

FIG. 12: Pharmacokinetic parameter estimates after IV bolus injection of the FSH analogue, β-hFSH-CTP-α-hFSH (r-hFSH-CTP), or the control recombinant hFSH protein (r-hFSH), each at a dose of 10 IU/kg.

FIG. 13: Mean pharmacokinetic parameter estimates after subcutaneous injection of the FSH analogue, β-hFSH-CTP-α-hFSH (r-hFSH-CTP), or the control recombinant hFSH protein (r-hFSH), each at a dose of 10 IU/kg.

FIG. 14: Amino acid sequence of β-hCG (SEQ ID NO:6), wherein CHO is a glycosylation site and the black shading corresponds to the CTP. N-linked glycosylation is present on Asn, and O-linked glycosylation is present on Ser.

FIG. 15: Schematic of the carbohydrate moieties on both hLH and hFSH and some of the microheterogeneity which results in the wide range of isoelectric points in the glycoprotein hormones.

FIG. 17: Nucleotide and amino acid sequence of β-hFSH. (SEQ ID NO:7). The signal sequence corresponds to the sequence beginning with the methionine at position 1 and ending with the cysteine at position 18.

FIG. 18: Nucleotide and amino acid sequence of α-hFSH. (SEQ ID NO:8). The signal sequence corresponds to the sequence beginning with the methionine at position 1 and ending with the serine at position 24.

FIG. 21: Mean pharmacokinetic parameters of serum hFSH following a single IV injection of either the control, recombinant human FSH (hFSH), FSH-CTP or N-2. Twenty-one day old female rats were injected at a dose of 2800 ng/rat.

DETAILED DESCRIPTION OF THE INVENTION

Figure 7:
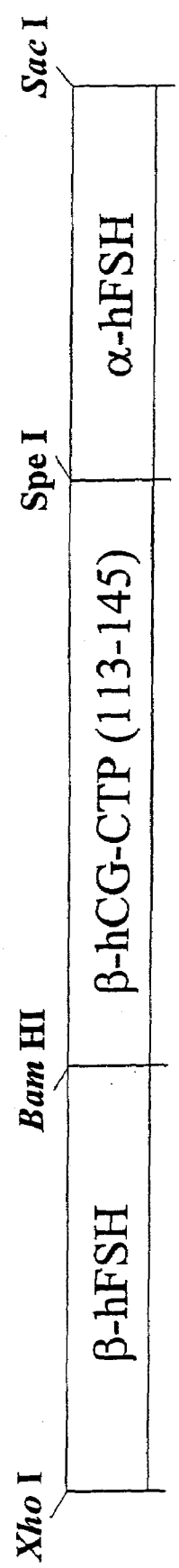
FIG. 7: Schematic of β-hFSH-CTP-α-hFSH construct with locations of restriction sites.

This invention provides FSH analogues, also referred to herein as "synthetic FSH." These analogues represent a significant advance over known agents for several reasons. Among these is the fact that these analogues can be expressed as single chain polypeptides having both the a and β subunits of FSH and a polypeptide segment having either O- or N-linked glycosylation sites. These single chain analogues are fully functional hormones that are more easily purified than analogues requiring separate expression and subsequent dimerization of the α and β subunits.

Also, the use of N-linked glycosylation sites in the polypeptide segment offers a number of advantages over the use of an hCG carboxy-terminal peptide sequence alone. Specifically, N-linked glycosylation sites are discreet and well-defined. This permits the facile construction of half-life-increasing moieties having one or more glycosylation sites at predetermined locations along a polypeptide, for example. Glycosylation using N-linked sites permits fine-tuning the half-life and thus the bioactivity of the instant synthetic hormones to meet particular therapeutic needs.

Definitions

The terms "amino acid," "amino acid residue" or "residue" are used interchangeably herein to refer to an amino acid that is incorporated into a protein, polypeptide or peptide. The amino acid can be, for example, a naturally occurring amino acid or an analog of a natural amino acid acid that can function in a similar manner as the naturally occurring amino acid.

As used herein, "CTP" means the carboxy-terminal peptide of β-hCG, corresponding to amino acid residues 113–145. This portion of hCG contains multiple O-linked glycosylation sites (see FIG. 14).

The letter "h" is used herein to designate the human isoform of a protein or polypeptide. For example, hFSH means human follicle stimulating hormone. FSH is a pituitary glycoprotein essential for follicular growth as well as spermatogenesis, comprised of a noncovalently linked heterodimer of two peptide subunits, α and β. The β subunit is specific to FSH and thus determines its biological activity, while the α subunit is common to the other members of this glycoprotein family, for example, luteinizing hormone (LH), chorionic gonadotrophin (CG) and thyroid-stimulating hormone (TSH).

The terms "nucleic acid", "polynucleotide" and "nucleic acid sequence" are used interchangeably herein, and each refers to a polymer of deoxyribonucleotides and/or ribonucleotides. The deoxyribonucleotides and ribonucleotides can be naturally occurring or synthetic analogues thereof.

The terms "polypeptide," "peptide" and "protein" are used interchangeably herein, and each means a polymer of amino acid residues. The amino acid residues can be naturally occurring or chemical analogues thereof. Polypeptides, peptides and proteins can also include modifications such as glycosylation, lipid attachment, sulfation, hydroxylation, and ADP-ribosylation.

As used herein, "serum half-life", abbreviated "$t_{1/2}$", means elimination half-life, i.e., the time at which the serum concentration of an agent has reached one-half its initial or maximum value. The term "increased serum halflife" used herein in reference to a synthetic agent means that the synthetic agent is cleared at a slower rate than either the non-synthetic, endogenous agent or the recombinantly produced version thereof. For example, the $t_{1/2}$ of a synthetic FSH, e.g., hFSH-N2, in a subject would be "increased" if it exceeds the $t_{1/2}$ of either endogenous FSH or recombinantly produced native FSH.

As used herein, "suitable host cells" include, but are not limited to, bacterial cells, yeast cells, fungal cells, insect cells, and mammalian cells. Mammalian cells can be transfected by methods well-known in the art such as calcium phosphate precipitation, electroporation and microinjection.

As used herein, "vector" means any nucleic acid vector known in the art. Such vectors include, but are not limited to, plasmid vectors, cosmid vectors, and bacteriophage vectors.

Units, prefixes and symbols may be denoted in their SI accepted form. Unless otherwise indicated, nucleic acid sequences are written left to right in 5' to 3' orientation and amino acid sequences are written left to right in amino- to carboxy-terminal orientation. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

In this invention, administering the instant pharmaceutical composition can be effected or performed using any of the various methods and delivery systems known to those skilled in the art. The administering can be performed, for example, intravenously, orally, via implant, transmucosally, transdermally, intramuscularly, and subcutaneously. In addition, the instant pharmaceutical compositions ideally contain one or more routinely used pharmaceutically acceptable carriers. Such carriers are well known to those skilled in the art. The following delivery systems, which employ a number of routinely used carriers, are only representative of the many embodiments envisioned for administering the instant composition.

Injectable drug delivery systems include solutions, suspensions, gels, microspheres and polymeric injectables, and can comprise excipients such as solubility-altering agents (e.g., ethanol, propylene glycol and sucrose) and polymers (e.g., polycaprylactones and PLGA's). Implantable systems include rods and discs, and can contain excipients such as PLGA and polycaprylactone.

Oral delivery systems include tablets and capsules. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

Transmucosal delivery systems include patches, tablets, suppositories, pessaries, gels and creams, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

Dermal delivery systems include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone).

Solutions, suspensions and powders for reconstitutable delivery systems include vehicles such as suspending agents (e.g., gums, zanthans, cellulosics and sugars), humectants (e.g., sorbitol), solubilizers (e.g., ethanol, water, PEG and propylene glycol), surfactants (e.g., sodium lauryl sulfate, Spans, Tweens, and cetyl pyridine), preservatives and antioxidants (e.g., parabens, vitamins E and C, and ascorbic acid), anti-caking agents, coating agents, and chelating agents (e.g., EDTA).

EMBODIMENTS OF THE INVENTION

This invention provides a first synthetic FSH comprising a β-FSH subunit, an α-FSH subunit and a half-life-increasing moiety, wherein the β-FSH subunit, α-FSH subunit and half-life-increasing moiety are covalently bound.

Half-life increasing moieties include, for example, a peptide containing one or more glycosylation sites. A half-life increasing moiety can also be nonpeptidyl, either in whole or in part, for example, polyethylene glycol.

In one embodiment of the instant invention, the β-FSH subunit and α-FSH subunit are bound to each other via the half-life-increasing moiety, and in a preferred embodiment, the β-FSH subunit, the α-FSH subunit and the polypeptide segment exist within a single polypeptide chain.

In one embodiment of the first synthetic FSH, the β-FSH subunit is bound at its C-terminal end to the N-terminal end of the polypeptide segment, and the polypeptide segment is bound at its C-terminal end to the N-terminal end of the α-FSH subunit. In another embodiment, the α-FSH subunit is bound at its C-terminal end to the N-terminal end of the polypeptide segment, and the polypeptide segment is bound at its C-terminal end to the N-terminal end of the β-FSH subunit. In a further embodiment, the synthetic FSH comprises the N-terminal signal sequence of either the β-FSH or α-FSH subunit.

In yet a further embodiment of the first synthetic FSH, the polypeptide segment comprises the carboxy-terminal portion of the β-hCG subunit. In the preferred embodiment, the carboxy-terminal portion of the β-hCG subunit comprises the amino acid sequence corresponding to positions 113–145 of the β-hCG subunit.

The carboxy-terminal portion of the β-hCG subunit is preferably glycosylated on one or more serine residues, constituting one or more O-linked glycosylation sites. This polypeptide segment can also comprise a region having one or more N-linked glycosylation sites.

As used herein, an "N-linked" glycosylation site includes, without limitation, asn followed by any of X-ser, X-thr and X-cys, wherein X is any amino acid except proline, and glycosylation occurs on the asn residue. In this invention, the amino acid sequence of any polypeptide situated N-terminal to, C-terminal to, or in between two N-linked sites, can be of any content and length needed to suit a particular design requirement.

The instant invention also provides a second synthetic FSH comprising a β-FSH subunit covalently bound to a polypeptide segment comprising the amino acid sequence ser-gly-ser-asn-ala-thr-gly-ser-gly-ser-asn-ala-thr-ser-gly-ser. (SEQ ID NO:9). The polypeptide segment may contain one or multiple copies of the amino acid sequence.

In one embodiment of the second synthetic FSH, the β-FSH subunit is bound at its C-terminal end to the N-terminal end of the peptide segment. In another embodiment, the β-FSH subunit is bound at its N-terminal end to the C-terminal end of the polypeptide segment.

This invention also provides a third synthetic FSH comprising a β-FSH subunit, an α-FSH subunit and a polypeptide segment comprising the amino acid sequence ser-gly-ser-asn-ala-thr-gly-ser-gly-ser-asn-ala-thr-ser-gly-ser, (SEQ ID NO:9), wherein the β-FSH subunit, α-FSH subunit and polypeptide segment are covalently bound.

In one embodiment of third synthetic FSH, the synthetic FSH comprises a β-FSH subunit bound at its C-terminal end to the N-terminal end of the α-FSH subunit. In another embodiment, the synthetic FSH comprises an α-FSH subunit bound at its C-terminal end to the N-terminal end of the polypeptide segment, or a β-FSH subunit bound at its C-terminal end to the N-terminal end of the polypeptide segment. Conversely, the synthetic FSH can comprise an α-FSH subunit bound at its N-terminal end to the C-terminal end of the polypeptide segment, or a β-FSH subunit bound at its N-terminal end to the C-terminal end of the polypeptide segment. In a further embodiment, the β-FSH subunit is bound at its C-terminal end to the N-terminal end of the polypeptide segment, which polypeptide segment is bound at its C-terminal end to the N-terminal end of the α-FSH subunit. In yet a further embodiment, the α-FSH subunit is bound at its C-terminal end to the N-terminal end of the β-FSH subunit. In another embodiment, the α-FSH subunit may be bound at its C-terminal end to the N-terminal end of the polypeptide segment, which polypeptide segment may be bound at its C-terminal end to the N-terminal end of the β-FSH subunit.

In certain embodiments of the instant synthetic FSHs, the glycosylation is either O-linked or N-linked glycosylation. The number of glycosylation sites may be any number, such as one, two, three, four, five, or six sites. In a preferred embodiment, each site is separated from its adjacent site by about six amino acid residues.

In an embodiment of any of the instant synthetic FSHs, the α-FSH subunit (if applicable) and β-FSH subunit are from an animal selected from the group consisting of a primate, a horse, a sheep, a bird, a bovine, a pig, a dog, a cat, and a rodent. In the preferred embodiment, the α-FSH and/or β-FSH subunit is a human subunit. In a further preferred embodiment, the α-FSH subunit (if applicable) and the β-FSH subunit exist within a single polypeptide chain along with the half-life-increasing moiety.

In a further embodiment of any of the instant synthetic FSHs, where the half-life increasing moiety is a polypeptide segment having the amino acid sequence ser-gly-ser-asn-ala-thr-gly-ser-gly-ser-asn-ala-thr-ser-gly-ser (SEQ ID NO:9), the polypeptide segment comprises one or a plurality of the amino acid sequence.

This invention also provides a pharmaceutical composition comprising one of the instant synthetic FSHs and a pharmaceutically acceptable carrier.

This invention further provides an article of manufacture comprising (a) the instant pharmaceutical composition, and (b) a label and/or instructions indicating a use of the pharmaceutical composition for the enhancement of fertility, egg production and/or spermatogenesis.

This invention provides nucleic acids encoding the instant synthetic FSH molecules, as well as expression vectors and suitable host cells for expressing said molecules. Examples of vectors include a plasmid, a cosmid, a λ phage and a yeast artificial chromosome, abbreviated "YAC". Any suitable cell system may be used to express the synthetic FSH molecules of the instant invention. For example, synthetic FSHs of the instant invention may be expressed in a bacterial cell or in a eukaryotic cell. In a preferred embodiment, a synthetic FSH is expressed in a Chinese hamster ovary cell, since this cell type provides certain advantageous post-translational protein modifications.

This invention also provides a method for producing a polypeptide that comprises growing a cell, for example a Chinese hamster ovary cell, under conditions permitting expression of the polypeptide encoded by the vector therein, and recovering the polypeptide so expressed. In a preferred embodiment, the vector encoding the polypeptide is transfected into the cells and subcultured under conditions that favor the growth of those cells which have taken up the vector. For example, the vector may contain one or more antibiotic resistance genes. Thus, medium containing the antibiotic will favor the growth of only those cells which have been transfected with the vector.

In a preferred embodiment, the polypeptide contains a signal sequence that targets the polypeptide for excretion from the cell. In a further embodiment, the excreted polypeptide may be collected, purified, and concentrated, for example by affinity chromatography, gel electrophoresis, and vacuum-assisted evaporation.

This invention also provides a method for producing a synthetic FSH, which comprises: (a) co-expressing (i) a nucleic acid which encodes an α-FSH subunit, and (ii) a nucleic acid which encodes a polypeptide comprising a β-FSH subunit and a polypeptide segment comprising the amino acid sequence ser-gly-ser-asn-ala-thr-gly-ser-gly-ser-asn-ala-thr-ser-gly-ser (SEQ ID NO:9), under conditions permitting such co-expression; and recovering the synthetic FSH so produced. In an embodiment of the instant invention, the polypeptide segment contains one or multiple copies of the amino acid sequence.

In one embodiment, the β-FSH subunit is bound at its C-terminal end to the N-terminal end of the polypeptide segment, or conversely, the β-FSH subunit is bound at its N-terminal end to the C-terminal end of the polypeptide segment.

This invention also provides a method for increasing a subject's fertility which comprises administering to the subject an amount of any of the instant synthetic FSHs effective to enhance the subject's fertility. Determining a therapeutically effective amount of the instant synthetic FSHs can be done based on animal data using routine computational methods.

In one embodiment, this method is used to enhance the efficiency of in vitro fertilization protocols. For example, a synthetic FSH of the instant invention can enhance the success of in vitro fertilization by stimulating follicular maturation and egg production in the subject.

In a preferred embodiment of the instant invention, the synthetic FSH is administered to the subject less frequently than current methods allow. For example, an FSH of the instant invention may be administered every other day, every 6 to 8 days, or weekly. The instant FSH can also be administered daily.

This invention also provides a method for increasing a subject's egg production which comprises administering to the subject an amount of a synthetic FSH of the instant invention effective to enhance the subject's egg production.

This invention further provides a method for increasing spermatogenesis in a subject through administering to the subject an amount of a synthetic FSH of the instant invention effective to enhance the subject's spermatogenesis.

As used herein, a subject can be, for example, a primate, a horse, a sheep, a bird, a bovine, a pig, a dog, a cat, or a rodent. In the preferred embodiment, the subject is a human.

Finally, this invention provides a method of increasing the half-life of a molecule in a subject, which method comprises glycosylating the molecule in a manner effective to increase the molecule's half-life.

In one embodiment, the molecule is a non-peptidyl organic molecule. In another embodiment, the molecule is a polypeptide. In a further embodiment, the glycosylation is either O-linked or N-linked glycosylation. The number and spacing of glycosylation sites is as set forth herein for the instant synthetic FSHs.

This invention is illustrated in the Experimental Details section which follows. This section is set forth to aid in an understanding of the invention but is not intended to, and should not be construed to, limit in any way the invention as set forth in the claims which follow thereafter.

EXPERIMENTAL DETAILS

Synopsis

This invention provides synthetic FSHs consisting of single chain fusions of β-hFSH, the common α-subunit, and an additional peptide moiety that provides an increased serum half-life while not interfering with biological activity. The pharmacokinetics, pharmacodynamics, and in vivo bioactivity of several examples of these synthetic FSHs in female rhesus monkeys are presented herein. The results demonstrate that both the absorption and the elimination half-lives of the instant synthetic FSHs are prolonged compared with native recombinant hFSH. Importantly, the analogues tested herein also demonstrated comparable in vitro bioactivity and enhanced in vivo activity compared with native recombinant hFSH.

Five examples of long-lasting FSH analogues are presented herein. These are: β-hFSH-N2 (FIG. 1), β-hFSH-N4 (FIG. 2), β-hFSH-CTP-αhFSH (FIG. 3), β-hFSH-N2-CTP-αhFSH (FIG. 4) and β-hFSH-N4-CTP-αhFSH (FIG. 5). Schematics of the CTP and N2/N4 constructs are shown in FIGS. 6 and 7. Detailed in vitro and in vivo bioactivity, as well as pharmacokinetic and pharmacodynamic analyses, were conducted for the latter three analogues and this data is presented in the section which follows.

Methods

General

Cloning and preparation of plasmid DNA were performed with *E. coli* strain DH5α. Clones were grown in standard Luria-Bertani medium (LB) for purification of recombinant DNA constructs. Transformation of DH5α was performed according to standard techniques using calcium chloride.

PCR reactions were performed with Vent DNA polymerase (New England Biolabs, Beverly, Mass.) and all products of the reactions were sequenced to ensure that no mutations were introduced during the amplification.

Construction of the β-hFSH-CTP-α Fusion Protein

A 5' primer introduced a Xho I site in the same frame and adjacent to the 5' ATG of the β-hFSH cDNA sequence whereas the 3' primer introduced an in frame Bam HI site adjacent to the codon for the last residue of the mature β-FSH which eliminated the terminator codon. In a similar fashion, a cDNA encoding the carboxy-terminal peptide of hCG (residues 113–145 of the hCG β-subunit sequence) was amplified with an in-frame Bam HI site adjacent to the codon for residue 113 and an in-frame Xba I site adjacent to the codon for residue 145. These two fragments were ligated to form a contiguous Xho I-Bam HI-Xba I β-hFSH-CTP fusion without a terminator codon at the 3' end. This fusion was then ligated to a cDNA encoding the mature α-subunit, lacking the amino-terminal signal peptide but including the terminator codon, flanked by in-frame 5' Spe I and 3' Sac I sites. The final construct encodes a fusion of the β-hFSH and α-subunit with the CTP sequence as the linker sequence. This final fusion sequence was then inserted into an SV40 expression vector.

Construction of the β-hFSH-N2/N4-α Fusion Protein

The β-hFSH-N2 and -N4 constructs consist of a single polypeptide chain hFSH molecule containing the β- and α-subunits tethered by a synthetic polypeptide consisting of either one or two tandem copies of the following: Ser-Gly- Ser-Asn-Ala-Thr-Gly-Ser-Gly-Ser-Asn-Ala-Thr-Ser-Gly-Ser. β-hFSH-N2 was constructed by synthesizing two complementary DNA strands encoding the above polypeptide in one of six potential reading frames. These two DNAs were designed such that following annealing a 5' Bam HI end and a 3' Spe I end were formed. The synthetic DNA duplex was then ligated into a vector with the hFSH β- and α-subunit encoding cDNAs. The in-frame ligation of these three DNAs was accomplished by placing a Xho I site immediately preceding the start codon and replacing the terminator codon of the hFSH β-subunit with a Bam HI site. In addition, an Spe I site was placed at the 5' end and a Sac I site immediately following the terminator codon of the α-subunit. The three fragments were then inserted into an SV40-based expression vector at Xho I/Sac I sites to form the β-hFSH-N2 expression construct. To insert a second copy of the synthetic polypeptide, a Bgl II site was inserted at the end of the synthetic sequence in the β-hFSH-N2 clone immediately preceding the Spe I site. The second copy of the synthetic polypeptide was then inserted by cleaving the β-hFSH-N2 construct with Bgl II and Spe I followed by insertion of the Bam HI/Spe I ended synthetic DNA to form β-hFSH-N4. This was feasible since Bam HI and Bgl II have identical cohesive termini.

Expression of β-hFSH Constructs

An SV40 expression clone containing the fusion construct was co-transfected into Chinese hamster ovary cells (CHO-K1) along with an SV2neo clone encoding resistance to the antibiotic G418. The CHO cell transformation was performed using a standard calcium phosphate precipitate technique. Selectable media containing G418 (Gemini Bioproducts, Woodland, Calif.) was used to select transfected cells. Isolated colonies were pooled and maintained in Ham's F-12 culture medium containing 500 ug/mL G418, 10% fetal bovine serum, 100 units/mL penicillin, 100 ug/mL streptomycin, and 4 mM glutamine. Pooled colonies were subcloned in 96 well microtiter dishes and clones were isolated that secreted about 3 pmole/mL of the fusion protein. To obtain higher yields, these cells were grown in suspension cultures, which produced about 9–14 pmole/mL.

Purification of β-hFSH Constructs

Spinner bottles were seeded at $10^5$ cells/mL in CHO-S-SFM medium (Life technologies, Rockville, Md.) containing 400 ug/mL G418. Cultures generally reached a density of $2\times10^6$ cells/mL on day 6 or 7, and the cell supernatant was harvested on day 7 or 8. PMSF was added to the supernatant at a concentration of 0.2 mM, which was then filtered through a 0.2 μm membrane and stored at 4° C. Affinity purification of was accomplished using an A201 (α-subunit specific antibody column). The column was prepared by coupling purified A201 immunoglobulins to CNBr-Sepharose-4B according to the manufacturer's instructions (Amersham Pharmacia Biotech, Piscataway, N.J.) at a concentration of 5 mg antibody/mL Sepharose. After applying the cell supernatant, the column was washed with 50 bed volumes of PBS followed by 2 bed volumes of distilled water. The fusion protein was eluted with 3–4 bed volumes of 1 M acetic acid and immediately dried on a Speed-Vac concentrator (Savant Instruments, Holbrook, N.Y.).

In Vitro FSH Bioactivity

Bioactivity of the hFSH analogues was evaluated using Y-1 cells transfected with the FSH receptor. Y-1 cell cultures were mixed with the fusion protein and native pituitary hFSH (control) at varying concentrations and media was assayed for cAMP activity as described in Bouloux et al, 2001.

Subcutaneous Protocol

Rhesus monkeys were injected subcutaneously with the fusion protein (n=4) or r-hFSH (Follistim, Organon Inc., n=2) at a dose of 10 IU/kg. All except 1 of the monkeys in each of the two treatment groups had been ovariectomized prior to injection. Serum hFSH was assayed prior to injection and at the following intervals post-injection: 12 h, 16 h, 20 h, 24 h, 36 h, 48 h, 60 h, and every 24 hours thereafter until levels reached baseline (approximately 9 days for control animals, 19–22 days for treatment animals).

Intravenous (IV) Protocol

One rhesus monkey was given an IV bolus of the fusion protein (10 IU/kg). A second animal was given an IV bolus of the control, r-hFSH at the same dose. Serum was assayed for hFSH prior to bolus administration and at the following intervals post-injection: 0.5 h, 1 h, 2 h, 4 h, 8 h, 12 h, 24 h, 36 h, 48 h, 72 h, 96 h, 120 h, 144 h and 168 h.

Pharmacokinetics

Recombinant human FSH (r-hFSH) (Follistim, Organon Inc, West Orange, N.J.) was used as a control. The Immulite assay (Diagnostic Products Corporation, Los Angeles, Calif.) was used to quantitate hFSH protein. This assay was able to detect the hFSH analogues in vitro and in vivo, and did not cross-react with rhesus FSH.

Pharmacokinetic Analysis

Each individual data set was evaluated by the pharmacokinetic data analysis program PKAnalyst (Micromath, Inc., Salt Lake City, Utah). For the IV dosing study, the following biexponential equation was fitted to the data: $C(t)=Ae-at+Be-bt$, where $C(t)$ is the plasma concentration at time "t", and A and B are the multiexponential coefficients. Values of a and b represent the initial-phase disposition rate constant and the terminal-phase disposition rate constant, respectively. PKAnalyst was used to generate the best-fit critical pharmacokinetic parameters, including elimination rate constant, half-life of initial (distribution) phase ($t_{1/2a}$), half-life of terminal (elimination) phase ($t_{1/2b}$), and total area under the blood concentration-time curve (AUC).

For the subcutaneous dosing studies, the blood concentration-time data were represented by the following biexponential equation: $C(t)=A(e-Ket-e-Kat)$, where $C(t)$ is the blood concentration at time "t" and A the multiexponential coefficient. Ke and Ka represent the elimination rate constant and absorption rate constant, respectively. All parameter estimates were computed by PKAnalyst. Bioavailability of r-hFSH and the hFSH analogues were estimated from the ratio of AUC (SC)/AUC (IV), at a constant dose (10 IU/kg).

In Vivo FSH Bioactivity

Ganirelix Acetate (250 μg) was administered by SC injection for 10 consecutive days to two normally cycling Rhesus monkeys beginning menstrual cycle day 4. The hFSH analogue was administered as a single subcutaneous dose (10 IU/kg) on cycle day 6. Venipuncture was performed daily and serum assayed for estradiol levels from cycle day 2 through cycle day 14. Serum estradiol was measured using an automated Immulite assay (Diagnostic Products Corporation, Los Angeles, Calif.).

Alternatively, hypophysectomized mice (surgery at 19 days) were purchased from the Charles River Company (Wilmington, Mass.). Upon arrival, mice were rehydrated with glucose-supplemented water for four days and randomized into control and experimental groups. Control recombinant hFSH protein or hFSH analogue was administered via a single subcutaneous injection in a total volume of 100 microliters at a dose of 10 IU. On day four post-injection, the animals were weighed and sacrificed by carbon dioxide asphyxiation followed by cardiopuncture and drainage. The uterus and ovaries were weighed and sectioned for histologic analysis.

Histologic Preparation and Follicle Counts

Both ovaries were removed from each animal. One ovary was weighed, immersed in formalin for fixation and embedded in paraffin according to standard protocols. Sections were cut at four to five micron intervals and every tenth section was stained with hematoxylin and eosin. Follicle density and maturation were assessed using the method of Pedersen and Peters (1968).

EXAMPLE 1

The β-hFSH-CTP-α Fusion Protein

In Vitro Bioactivity

Figure 8:
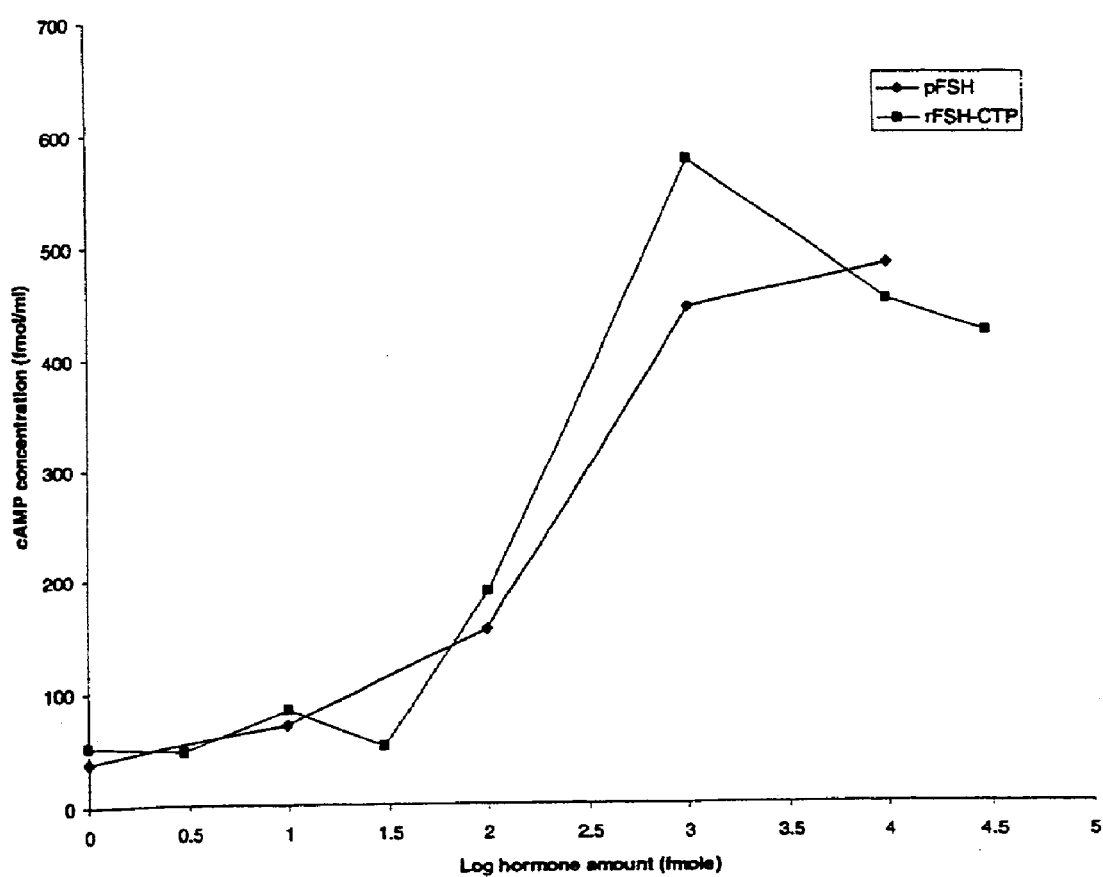
FIG. 8: In vitro bioassay of hormone activity. cAMP concentration (fmol/ml) was quantitated in Y1 cells expressing the FSH receptor after treatment with the indicated amount of either pituitary FSH (pFSH) or the FSH analogue, β-hFSH-CTP-α-hFSH (rFSH-CTP).

The bioactivity of the β-hFSH-CTP-α analogue was first assessed by an assay of hFSH receptor activity. In this assay, a recombinant native hFSH receptor is expressed in a suitable host cell and cAMP induction is measured following incubation with hormone (Lindau-Shepard et al, 2001). As shown in FIG. 8, the β-hFSH-CTP-α analogue induced a similar rise in cAMP levels when compared with recombinant hFSH, demonstrating that this single-chain fusion analogue folded properly into an unhindered, biologically active hormone.

Pharmacokinetics

In order to establish the pharmacokinetic parameters of the instant synthetic FSH, Rhesus monkeys were injected with an IV bolus dose (10 IU/kg) of either a recombinant native hFSH, or the β-hFSH-CTP-α analogue. The serum concentration of hFSH was determined by immunoassay at times following injection and a serum concentration-time curve was generated based on the data. For both the recombinant native hFSH and the β-hFSH-CTP-α analogue, the resulting curve fit a two-compartment model, consisting of an initial distribution half-life and a second, slower, elimination half-life. As indicated by the pharmacokinetic parameter estimates listed in FIG. 12, the half-life of elimination for the β-hFSH-CTP-α analogue was more than four-fold longer than that of the native hFSH.

Figure 9:
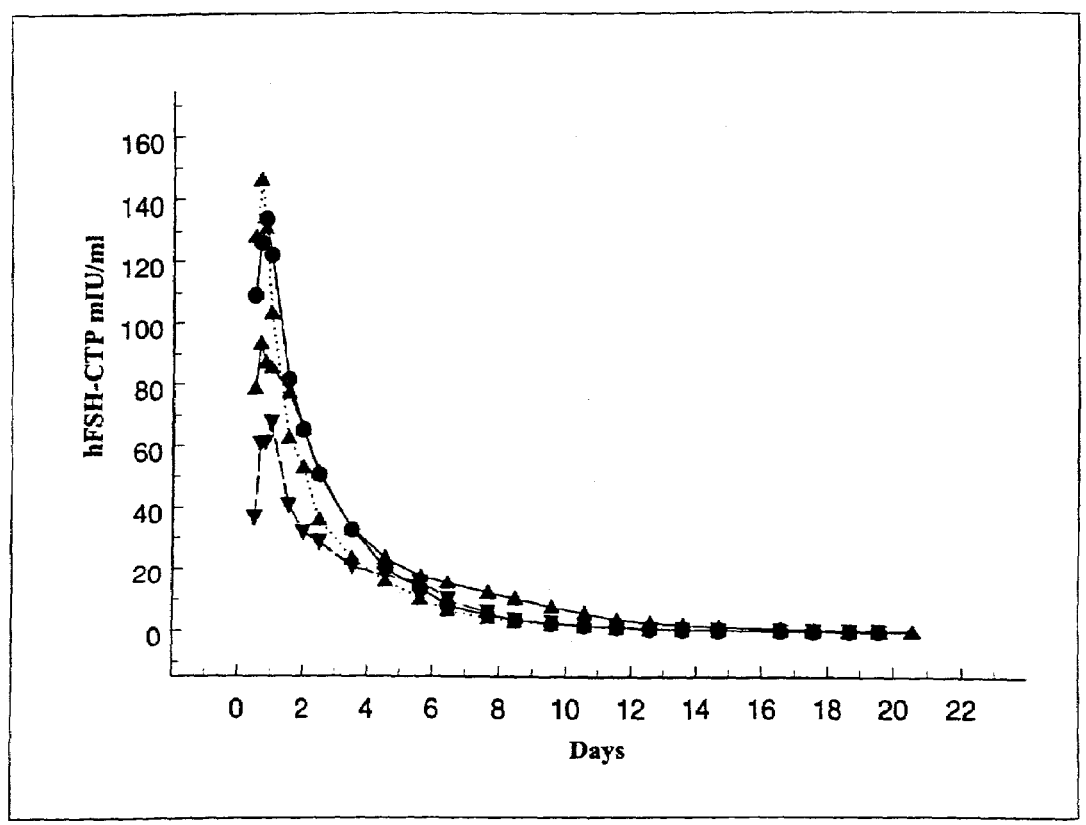
FIG. 9: Serum levels of the FSH analogue, β-hFSH-CTP-α-hFSH (hFSH-CTP), in 4 rhesus monkeys (indicated by triangles, inverted triangles, circles, and squares, respectively) measured at the indicated times following a single subcutaneous injection at a dose of 10 IU/kg.
Figure 10:
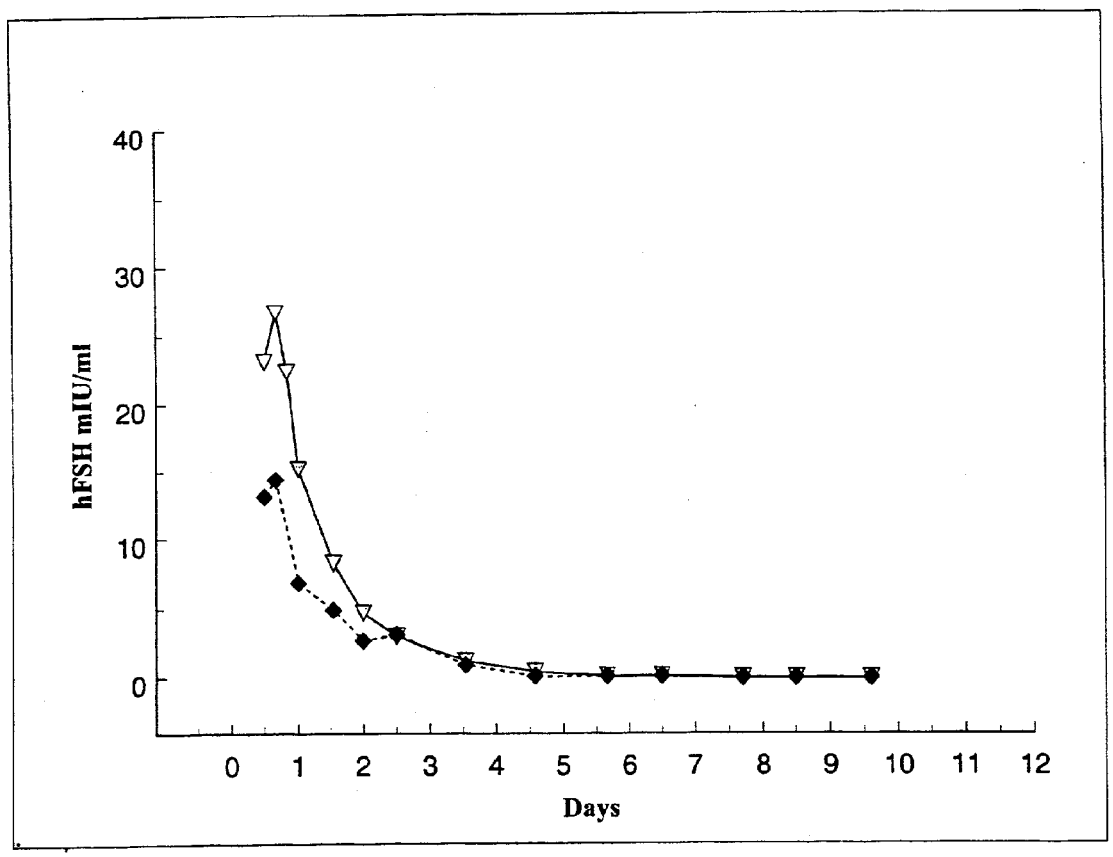
FIG. 10: Serum levels of the control recombinant hFSH protein, (hFSH), in 2 rhesus monkeys (indicated by diamonds and triangles, respectively) measured at the indicated times following a single subcutaneous injection at a dose of 10 IU/kg.

Although these results obtained following an intravenous bolus injection were encouraging, it was also important to determine the pharmacokinetic parameters of the synthetic FSH following a subcutaneous injection. This is because subcutaneous administration is a relatively easier route for clinical use. As indicated by the serum concentration-time curves for treatment animals (n=4) receiving the βhFSH-CTP-α analogue (FIG. 9) and controls (n=2) receiving native hFSH (FIG. 10), the serum levels of native hFSH approached baseline by day 4 post-injection, whereas elevated (>2 mIU/mL) levels of the β-hFSH-CTP-α analogue were maintained for approximately 10 days. These data fit a one-compartment pharmacokinetic model, the parameter estimates of which are given in FIG. 13. Notably, the half-life of absorption for the instant synthetic FSH was approximately threefold longer than that of the native hFSH. These results show that the half-life of elimination correlates well with the intravenous data and confirms the slower metabolism and clearance of the β-hFSH-CTP-α analogue. Addition of the CTP moiety to hFSH thus induced a depot effect, retarding the absorption of the product following subcutaneous administration. This explains the slower time to reach peak concentration ($t_{max}$) for animals receiving the β-hFSH-CTP-α analogue. As indicated in FIG. 13, both drugs were highly bioavailable after subcutaneous administration.

In Vivo Bioactivity

Figure 11:
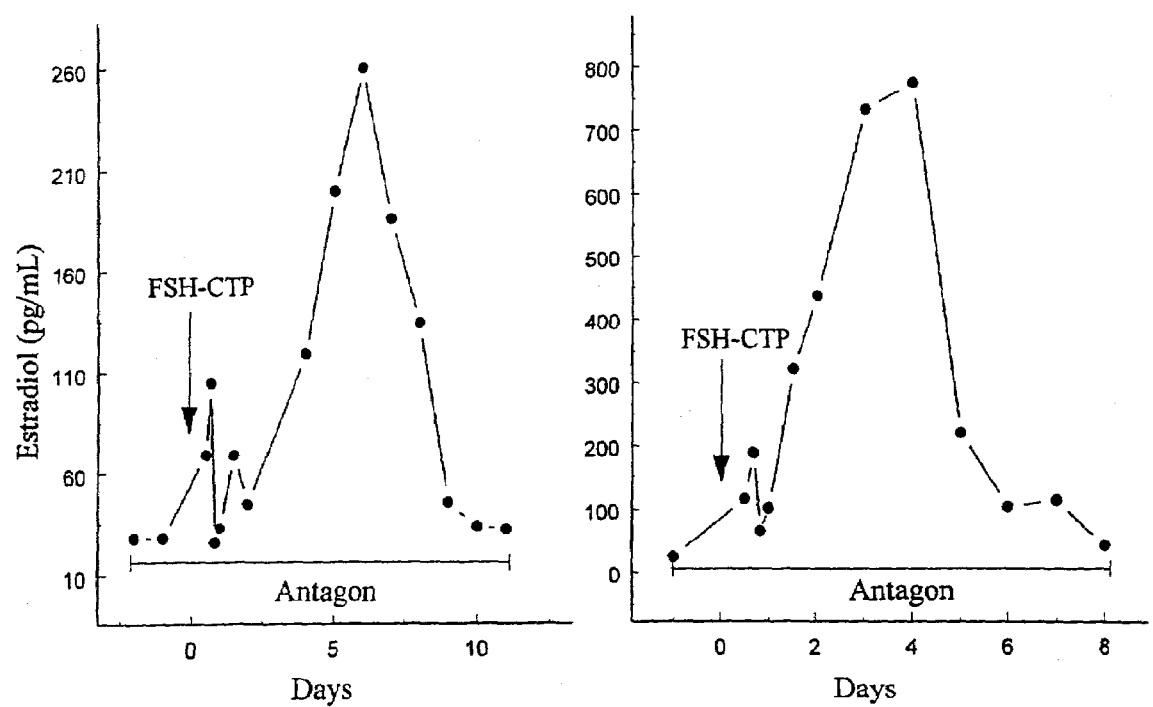
FIG. 11: Serum estradiol levels in two normally cycling monkeys following a single subcutaneous injection of the FSH analogue, β-hFSH-CTP-α-hFSH (FSH-CTP). The time of injection is indicated by arrows. Both monkeys were given the GnRH antagonist Ganirelix Acetate for the duration of the study.
Figure 16:
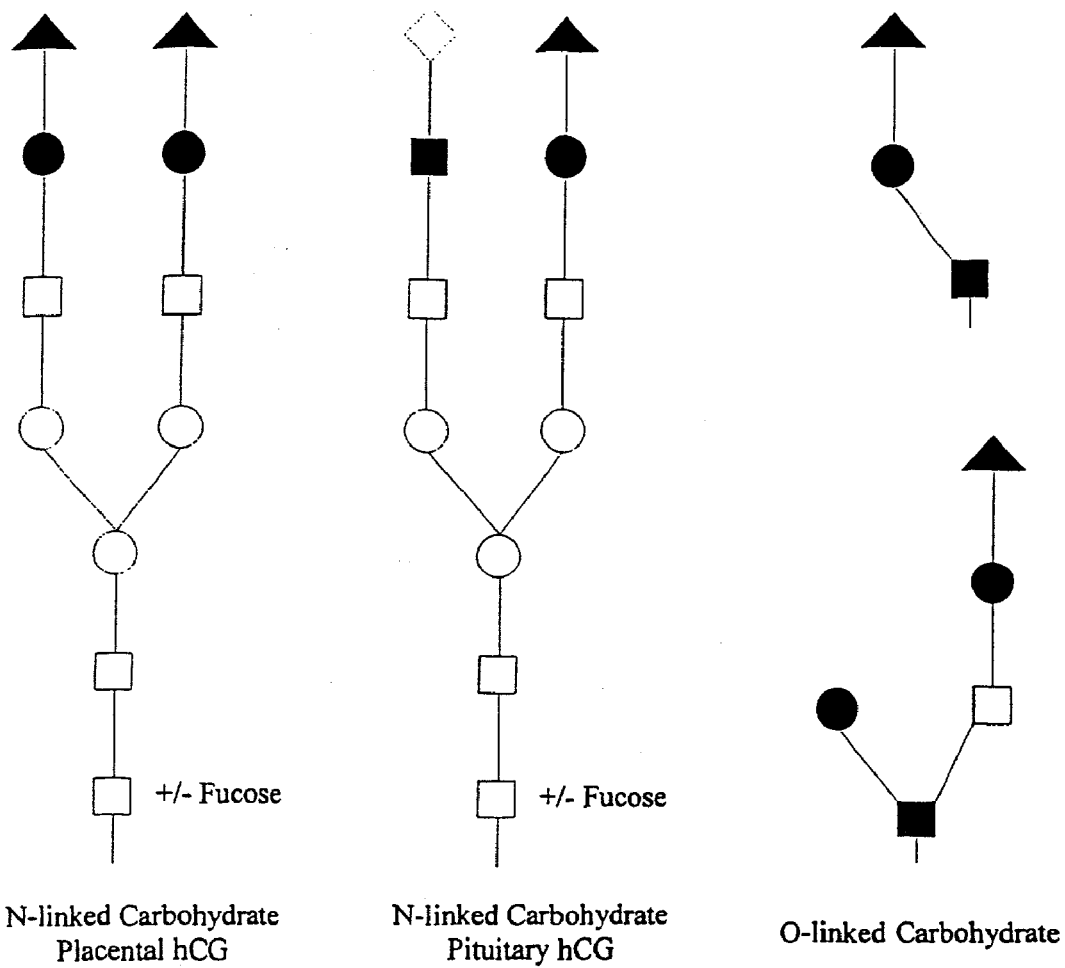
FIG. 16: Schematic examples of N-linked and O-linked carbohydrates.

To establish the bioactivity of the β-hFSH-CTP-α analogue in vivo, two normally cycling monkeys were injected with a single dose of the analogue, and serum was assayed for estradiol at various times following injection. Both monkeys were given a GnRH antagonist (Antagon, Organon, West Orange, N.J.) for the duration of the study, eliminating any effect on ovarian estrogen production from endogenous Rhesus FSH. As shown in FIG. 11, serum estradiol levels initially increased in both animals, with peak levels achieved at 3 and 5 days post-injection. One monkey attained supraphysiologic levels of estradiol (peak 773 pg/mL) on day 4 post-injection, suggesting early recruitment of multiple follicles. Thus, the β-hFSH-CTP-α analogue demonstrated similar, and in one case substantially increased, in vivo biological activity compared to native hFSH.

Conclusions

The results presented herein demonstrate that the addition of CTP to the carboxy terminus of the β subunit of hFSH had no adverse impact on folding of the molecule, receptor binding, or in vitro signal transduction. Furthermore, the fusion protein was metabolized at a slower rate than the native hormone, as circulating levels remained elevated for an extended period of time compared to native recombinant hFSH. Quantitatively, the half-life of elimination for the β-hFSH-CTP-α analogue following subcutaneous administration was 2 to 3 times longer than that of native recombinant hFSH. This difference corresponds well with the only previous report on pharmacokinetics in humans, which was done with male subjects, in which the half-life of elimination after subcutaneous administration was prolonged by a similar magnitude compared with historic controls receiving native hormone.

These results also confirm the accuracy of our parameter estimate for elimination half-life by assessing pharmacokinetics after IV administration. Surprisingly, absorption of the β-hFSH-CTP-α analogue was delayed by approximately three-fold following subcutaneous administration. The long circulating presence of the β-hFSH-CTP-α analogue after subcutaneous administration is thus explained not only by a decreased metabolism of the protein, but by a depot effect resulting in slower absorption.

In summary, the pharmacodynamics and biological activity of a β-hFSH-CTP-α analogue in a primate model are described herein for the first time. Administration of the β-hFSH-CTP-α analogue to 2 monkeys given a GnRH antagonist (to suppress endogenous FSH activity) elicited a dramatic rise in serum estradiol levels. A single subcutaneous dose resulted in elevated estradiol levels for 5–7 days, with one monkey achieving a peak estradiol level greater than 3 times that seen during a normal endogenous Rhesus cycle. This supraphysiologic response is indicative of multifollicular recruitment, although sonographic confirmation was not performed. Such prolonged elevations in estradiol are not normally seen after isolated subcutaneous injections of native recombinant hFSH.

These results confirm the feasibility of achieving prolonged ovarian stimulation following a single injection of a recombinant gonadotropin analogue. Fewer injections will result in less patient discomfort, improved compliance, and possibly a reduction in the number of local side effects.

Combination therapy using both long and short-acting FSH formulations, either together and/or sequentially during a stimulation cycle, should also be considered. In these cases, the short-acting (native) formulation may be used to "fine-tune" the FSH dose after an initial bolus of a long-acting analog.

Ideal candidates for treatment with long-acting FSH analogues include infertile males with hypogonadotropic hypogonadism, who typically require prolonged courses of gonadotropin therapy. This technology also provides a significant improvement over current methods for stimulating follicular maturation and egg production in a subject being treated for infertility and for in vitro fertilization protocols.

EXAMPLE 2

The β-hFSH-N2/N4-α Fusion Protein

In Vitro Bioactivity

The bioactivity of the β-hFSH-N2/N4-α analogues was first assessed by an assay for hFSH receptor activation as discussed above. The N2/N4 analogue induced a similar rise in cAMP levels when compared with native hFSH, demonstrating that, like the CTP analogue discussed above, this single-chain fusion protein folded properly into an unhindered, biologically active hormone.

Pharmacokinetics

Figure 20:
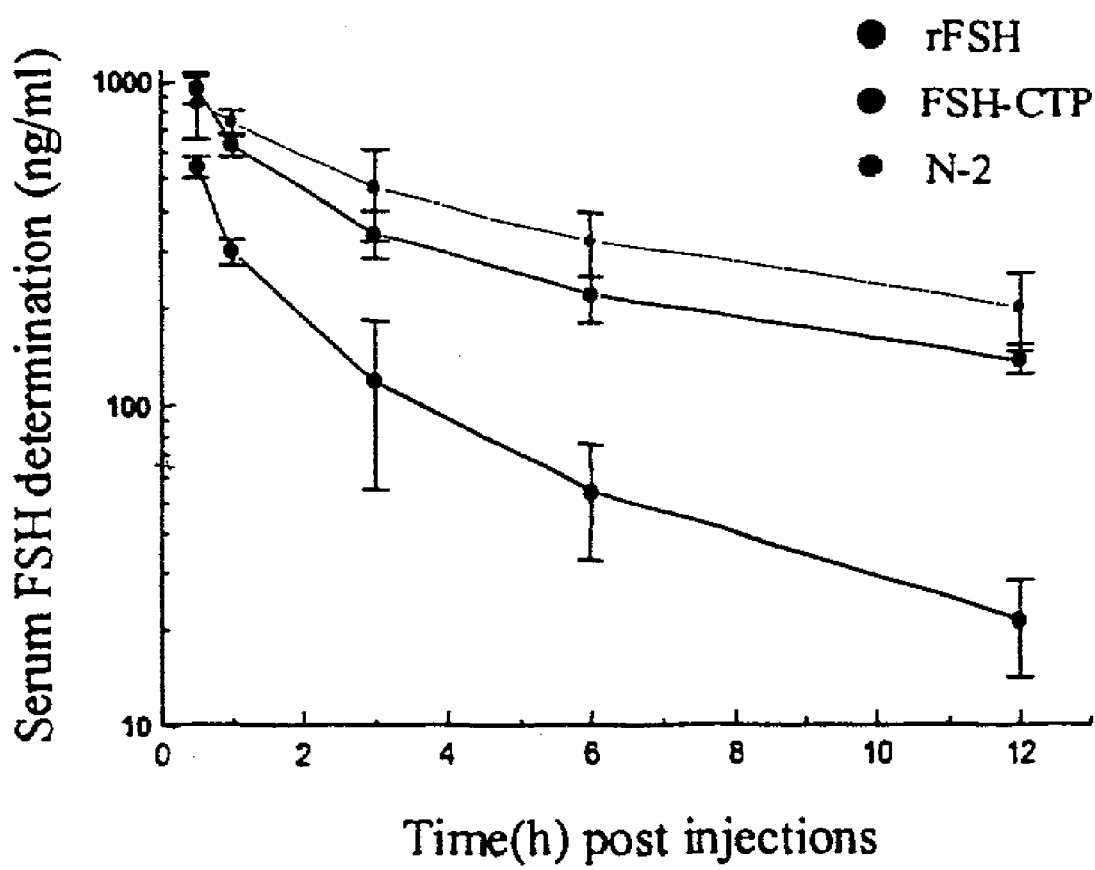
FIG. 20: Mean serum hFSH concentration-time profiles following a single IV injection of either recombinant human FSH (rFSH), FSH-CTP or N-2. Twenty-one day old female rats were injected at a dose of 2800 ng/rat.

Pharmacokinetic analysis was performed using twelve immature female rats divided into four groups of 3 each. Each of the three proteins (hFSH, hFSH-CTP, hFSH-N2) was diluted to 11 µg/ml in injection buffer containing BSA (1 mg/ml), and given as a single intravenous dose of 2800 ng/rat in 0.25 ml of buffer. The control group received 0.25 ml of saline (data not shown). Serum was assayed at the following intervals post-injection: 0.5, 1.0, 3.0, 6.0, and 12 hours. The serum concentration-time curves are shown in FIG. 20. For all products the curves could be explained by a two-compartment model, with an initial half-life reflecting the distribution phase, and a second, slower elimination half-life. As indicated by the pharmacokinetic parameter estimates in FIG. 21, the half-life of elimination for the synthetic FSHs, hFSH-CTP and hFSH-N2, was approximately two-fold longer than that of native hFSH (3.5 h vs 7.1 and 6.3 h, respectively).

In Vivo Bioactivity

Figure 19:
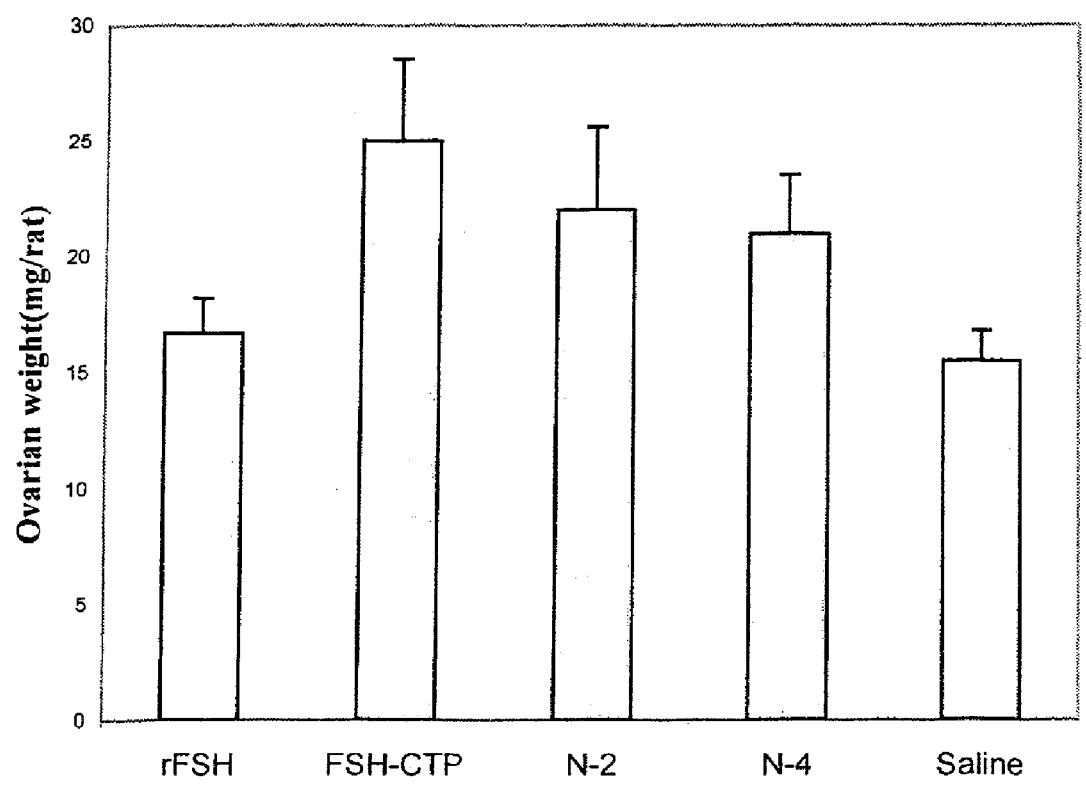
FIG. 19: Mean ovarian weight three days following subcutaneous injection of either recombinant human FSH (rFSH), FSH-CTP, N-2, N4, or saline.

An ovarian weight gain assay was used to assess the relative in vivo bioactivity of the control, recombinant native FSH (rFSH) and the CTP and N2 FSH analogues. The compounds were administered in a single subcutaneous injection. The mean ovarian weights as determined on day three following injection are shown in FIG. 19.

Pharmacodynamics

The pharmacodynmacis of the N2/N4 analogues were assessed by a determination of ovarian weight change in immature female rats following a single subcutaneous injection of either a recombinant native hFSH, the CTP, the N2, or the N4 analogue. The results of these analyses are summarized in FIG. 19. The data indicated that the mean ovarian weights three days post-injection were significantly higher for the CTP, N2 and N4 analogues compared with the native hFSH control or saline.

Conclusions

The results described herein demonstrate that the addition of N-linked carbohydrates imparts a longer half-life to native hFSH, thereby increasing its bioactivity in a manner analogous to that conferred by the O-linked sugars on the CTP.

These results further demonstrate that a synthetic sequence bearing artificial N-linked glycosylation consensus sequences can be efficiently glycosylated in cultured cells. This in turn demonstrates the feasibility of producing synthetic FSH having improved stability and bioactivity through directed modifications of glycosylation patterns via the addition of artificial sequences.

REFERENCES

Bouloux, P. M., D. J. Handelsman, F. Jockenhovel, E. Nieschlag, J. Rabinovici, W. L. Frasa, J. J. de Bie, G. Voortman, and J. Itskovitz-Eldor (2001) First human exposure to FSH-CTP in hypogonadotrophic hypogonadal males. *Hum. Reprod.* 16, 1592–1597.

Calvo, F. O., H. T. Keutmann, E. R. Bergert, and R. J. Ryan (1986) Deglycosylated human follitropin: characterization and effects on adenosine cyclic 3',5'-phosphate production in porcine granulosa cells. *Biochemistry* 25, 3938–3943.

Fares, F. A., N. Suganuma, K. Nishimori, P. S. Lapolt, A. J. Hsueh, and I. Boime (1992) Design of a long-acting follitropin agonist by fusing the C-terminal sequence of the chorionic gonadotropin beta subunit to the follitropin beta subunit. *Proc. Natl. Acad. Sci. U.S.A.* 89, 4304–4308.

Feng, W., M. M. Matzuk, K. Mountjoy, E. Bedows, R. W. Ruddon, and I. Boime (1995) The asparagine-linked oligosaccharides of the human chorionic gonadotropin beta subunit facilitate correct disulfide bond pairing. *J. Biol. Chem.* 270, 11851–11859.

Krichevsky, A., S. Birken, J. F. O'Connor, K. Bikel, J. Schlatterer, and R. E. Canfield (1994) The development of a panel of monoclonal antibodies to human luteinizing hormone and its application to immunological mapping and two-site assays. *Endocrine* 2, 511–520.

LeContonnec, J. Y., H. C. Porchet, V. Beltrami, A. Khan, S. Toon, and M. Rowland (1994) Clinical pharmacology of recombinant human follicle-stimulating hormone. II. Single doses and steady-state pharmacokinetics. *Fertil. Steril.* 61, 679–86.

Lindau-Shapard, B. A., H. A. Brumberg, A. J. Peterson, and J. A. Dias (2001) Reversible immunoneutralization of human follitropin receptor. *J. Reprod. Immun.* 49, 1–19.

Matzuk, M. M., A. J. Hsueh, P. Lapolt, A. Tsafriri, J. L. Keene, and I. Boime (1990) The biological role of the carboxyl-terminal extension of human chorionic gonadotropin beta-subunit. *Endocrinology* 126, 376–383.

Pedersen, T. and H. Peters (1968) Proposal for a classification of oocytes and follicles in the mouse ovary. *J. Reprod. Fertil* 17, 555–557.

Pierce, J. G. and T. F. Parsons (1981) Glycoprotein hormones: structure and function. *Annu. Rev. Biochem.* 50, 465–495.

Porchet, H. C., J. Y. LeContonnec, B. Neuteboom, S. Canali, and G. Zanolo (1995) Pharmacokinetics of recombinant human luteinizing hormone. *J. Clin. Endocrinol. Metab.* 80, 667–73.

Sairam, M. R. and P. Manjunath (1982) Studies on pituitary follitropin. XL Induction of hormonal antagonistic activity by chemical deglycosylation. *Mol. Cell Endocrinol.* 28, 139–150.

Saal, W., H. J. Glowania, and J. Happ (1991) Pharmacodynamics and pharmacokinetics after subcutaneous and intramuscular injection of human chorionic gonadotropin. *Fertil. Steril.* 56, 225–8.

Suganuma, N., M. M. Matzuk, and I. Boime (1989) Elimination of disulfide bonds affects assembly and secretion of the human chorionic gonadotropin beta subunit. *J. Biol. Chem.* 264, 19302–19307.

Yen, S. S., O. Llerena, B. Little, and O. H. Pearson (1968) Disappearance rates of endogenous luteinizing hormone and chorionic gonadotropin in man. *J. Clin. Endocrinol. Metab* 28, 1763–1767.

What is claimed is:

1. A synthetic FSH comprising a β-FSR subunit covalently bound to a polypeptide segment comprising the amino acid sequence ser-gly-ser-asn-ala-thr-gly-ser-gly-ser-asn-ala-thr-ser-gly-ser (SEQ ID NO:9).

2. A synthetic FSH comprising a β-FSH subunit, an α-FSH subunit and a polypeptide segment comprising the amino acid sequence ser-gly-ser-asn-ala-thr-gly-ser-gly-ser-asn-ala-thr-ser-gly-ser (SEQ ID NO:9), wherein the β-FSH subunit, α-FSH subunit and polypeptide segment are covalently bound.

3. A method for producing a synthetic FSH, which method comprises:
   (a) co-expressing (i) a nucleic acid which encodes an α-FSH subunit, and (ii) a nucleic acid which encodes a polypeptide comprising a β-FSH subunit and a polypeptide segment comprising the amino acid sequence ser-gly-ser-asn-ala-thr-gly-ser-gly-ser-asn-ala-thr-ser-gly-ser (SEQ ID NO:9), under conditions permitting such co-expression; and
   (b) recovering the synthetic FSH so produced.

4. The synthetic FSH of claim 1 wherein the β-FSH subunit is from an animal selected from the group consisting of a primate, a horse, a sheep, a bird, a bovine, a pig, a dog, a cat and a rodent.

5. The synthetic FSH of claim 4, wherein the β-FSH subunit is a human β-FSH subunit.

6. The synthetic FSH of claim 1, wherein the β-FSH subunit and the polypeptide segment exist within a single polypeptide chain.

7. The synthetic FSH of claim 1, wherein the polypeptide segment contains one copy of the amino acid sequence set forth in SEQ ID NO:9.

8. The synthetic FSH of claim 1, wherein the polypeptide segment comprises a plurality of the amino acid sequence set forth in SEQ ID NO:9.

9. The synthetic FSH of claim 1, wherein the β-FSH subunit is bound at its C-terminal end to the N-terminal end of the peptide segment.

10. The synthetic FSH of claim 1, wherein the β-FHS subunit is bound at its N-terminal end to the C-terminal end of the polypeptide segment.

11. The synthetic FSH of claim 2, wherein the α-FSH and β-FSH subunits are from an animal selected from the group consisting of a primate, a horse, a sheep, a bird, a bovine, a pig, a dog, a cat and a rodent.

12. The synthetic FSH of claim 11, wherein the α-FSR and β-FHS subunits are human α-FSH and β-FSH subunits.

13. The synthetic FSH of claim 2, wherein the β-FSH subunit, α-FSH subunit and polypeptide segment exist within a single polypeptide chain.

14. The synthetic FSH of claim 2, wherein the polypeptide segment contains one copy of the amino acid sequence set forth in SEQ ID NO:9.

15. The synthetic FSH of claim 2, wherein the polypeptide segment comprises a plurality of the amino acid sequence set forth in SEQ ID NO:9.

16. The synthetic FSH of claim 2, wherein the β-FSH subunit is bound at its C-terminal end to the N-terminal end of the α-FSH subunit.

17. The synthetic FSH of claim 2, wherein the α-FSH subunit is bound at its C-terminal end to the N-terminal end of the polypeptide segment.

18. The synthetic FSH of claim 2, wherein the β-FSH subunit is bound at its N-terminal end to the C-terminal end of the polypeptide segment.

19. The synthetic FSH of claim 2, wherein the β-FHS subunit is bound at its C-terminal end to the N-terminal end of the polypeptide segment, which polypeptide segment is bound at its C-terminal end to the N-terminal end of the α-FSH subunit.

20. The synthetic FSH of claim 2, wherein the α-FSH subunit is bound at its C-terminal end to the N-terminal end of the β-FSH subunit.

21. The synthetic FSH of claim 2, wherein the β-FSH subunit is bound at its C-terminal end to the N-terminal end of the polypeptide segment.

22. The synthetic FSH of claim 2, wherein the α-FSR subunit is bound at its N-terminal end to the C-terminal end of the polypeptide segment.

23. The synthetic FSH of claim 2, wherein the α-FSH subunit is bound at its C-terminal end to the N-terminal end of the polypeptide segment, which polypeptide segment is bound at its C-terminal end to the N-terminal end of the β-FHS subunit.

24. The method of claim 3, wherein the α-FSH and β-FSH subunits are from an animal selected from the group consisting of a primate, a horse, a sheep, a bird, a bovine, a pig, a dog, a cat and a rodent.

25. The method of claim 24, wherein the α-FSH and β-FSH subunits are human α-FSH and β-FSH subunits.

26. The method of claim 3, wherein the polypeptide segment contains one copy of the amino acid sequence set forth in SEQ ID NO:9.

27. The method of claim 3, wherein the polypeptide segment comprises a plurality of the amino acid sequence set forth in SEQ ID NO:9.

28. The method of claim 3, wherein the β-FSH subunit is bound at its C-terminal end to the N-terminal end of the polypeptide segment.

29. The method of claim 3, wherein the β-FHS subunit is bound at its N-terminal end to the C-terminal end of the polypeptide segment.

* * * * *